US008858952B2

(12) United States Patent
Knutson

(10) Patent No.: US 8,858,952 B2
(45) Date of Patent: Oct. 14, 2014

(54) METHODS AND MATERIALS FOR GENERATING T CELLS

(75) Inventor: Keith L. Knutson, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 384 days.

(21) Appl. No.: 13/202,263

(22) PCT Filed: Feb. 19, 2010

(86) PCT No.: PCT/US2010/024792
§ 371 (c)(1),
(2), (4) Date: Aug. 18, 2011

(87) PCT Pub. No.: WO2010/096693
PCT Pub. Date: Aug. 26, 2010

(65) Prior Publication Data
US 2011/0311566 A1 Dec. 22, 2011

Related U.S. Application Data

(60) Provisional application No. 61/153,771, filed on Feb. 19, 2009.

(51) Int. Cl.
| | | |
|---|---|---|
| A61K 39/00 | (2006.01) | |
| A61K 39/385 | (2006.01) | |
| A61K 45/00 | (2006.01) | |
| C07K 5/103 | (2006.01) | |
| C07K 14/74 | (2006.01) | |
| C12N 5/0783 | (2010.01) | |
| C07K 7/08 | (2006.01) | |

(52) U.S. Cl.
CPC ....... C07K 14/70539 (2013.01); C07K 2319/33 (2013.01); A61K 2039/64 (2013.01); A61K 2039/6031 (2013.01); A61K 39/385 (2013.01); C07K 2319/01 (2013.01); C07K 5/101 (2013.01); C07K 7/08 (2013.01); C12N 2501/998 (2013.01); C07K 2319/50 (2013.01); A61K 2039/5158 (2013.01); C12N 5/0636 (2013.01)
USPC ................ 424/185.1; 424/192.1; 424/277.1; 424/278.1

(58) Field of Classification Search
None
See application file for complete search history.

(56) References Cited

U.S. PATENT DOCUMENTS

| | | | |
|---|---|---|---|
| 4,237,224 A | 12/1980 | Cohen et al. | |
| 4,273,875 A | 6/1981 | Manis | |
| 4,363,877 A | 12/1982 | Goodman et al. | |
| 4,428,941 A | 1/1984 | Galibert et al. | |
| 4,431,739 A | 2/1984 | Riggs | |
| 6,326,465 B1 | 12/2001 | Hess | |
| 6,440,735 B1 | 8/2002 | Gaeta | |
| 6,734,014 B1 | 5/2004 | Hwu et al. | |
| 8,372,409 B2* | 2/2013 | Mohamadzadeh | 424/202.1 |
| 2009/0060936 A1* | 3/2009 | Humphreys et al. | 424/193.1 |

FOREIGN PATENT DOCUMENTS

WO WO 01/87325 11/2001

OTHER PUBLICATIONS

Bayrak et al., "T cell response of I-Aq mice to self type II collagen: meshing of the binding motif of the I-Aq molecule with repetitive sequences results in autoreactivity to multiple epitopes," Int. Immunol., 9(11):1687-1699, Nov. 1997.
Knutson and Disis, "Clonal diversity of the T-cell population responding to a dominant HLA-A2 epitope of HER-2/neu after active immunization in an ovarian cancer patient.," Hum. Immunol., 63(7):547-557, Jul. 2002.
Knutson et al., "T-cell immunity to the folate receptor alpha is prevalent in women with breast or ovarian cancer," J. Clin. Onc., 24(26):4254-4261, print Sep. 2006, Epub Aug. 2006.
Krysan et al., "Quantitative characterization of furin specificity. Energetics of substrate discrimination using an internally consistent set of hexapeptidyl methylcoumarinamides.," J. Biol. Chem., 274(33):23229-23234, Aug. 1999.
McFarland et al., "Energetic asymmetry among hydrogen bonds in MHC class II*peptide complexes," Proc. Natl. Acad. Sci. USA, 98(16):9231-9236, Jul. 2001.
Nava-Parada et al., "Peptide vaccine given with a Toll-like receptor agonist is effective for the treatment and prevention of spontaneous breast tumors," Cancer Res., 67(3):1326-1334, Feb. 2007.
Radhakrishnan et al., "B7-DC cross-linking restores antigen uptake and augments antigen-presenting cell function by matured dendritic cells.," Proc. Natl. Acad. Sci. USA, 102(32):11438-11443, Aug. 2005 with retraction Proc. Natl. Acad. Sci. USA., 107(18): 8498, May 2010.
Surman et al., "Cutting edge: CD4+ T cell control of CD8+ T cell reactivity to a model tumor antigen," J. Immunol., 164(2):562-565, Jan. 2000.
Tam et al., "An SN2 deprotection of synthetic peptides with a low concentration of hydrofluroric acid in dimethyl sulfide: evidence and application in peptide synthesis," J. Am. Chem. Soc., 105(21):6442-6455, Oct. 1983.
Thomas, "Furin at the cutting edge: from protein traffic to embryogenesis and disease," Nat. Rev. Mol. Cell Biol., 3(10):753-766, Oct. 2002.

(Continued)

Primary Examiner — Gerald R Ewoldt
Assistant Examiner — Marianne Dibrino
(74) Attorney, Agent, or Firm — Fish & Richardson P.C.

(57) ABSTRACT

The document provides to methods and materials for generating T cells (e.g., antigen-specific CD4+ T cells). For example, methods and materials for using nested MHC class II epitopes as vaccines to generate activated CD4+ T cells in vivo or as reagents to generate activated CD4+ T cells ex vivo are provided.

1 Claim, 29 Drawing Sheets

(56) References Cited

OTHER PUBLICATIONS

Wettstein et al., "The application of real-time PCR to the analysis of T cell repertoires," *Nucleic Acid Res.*, 36(21):e140, Epub Oct. 2008.
International Search Report and Written Opinion for PCT/US2010/024792, mailed Nov. 19, 2010, 11 pages.
International Preliminary Report on Patentability for PCT/US2010/024792, mailed Sep. 1, 2011, 6 pages.
Gillogly et al., "Ii-Key/HER-2/neu MHC class-II antigenic epitope vaccine peptide for breast cancer," Cancer Immunol Immunother., 53(6):490-496, Epub Jan. 22, 2004.
Humphreys et al., "Increasing the potency of MHC class II-presented epitopes by linkage to Ii-Key peptide," Vaccine, 18(24):2693-2697, Jun. 1, 2000.
Kallinteris et al., "Enhanced CD4+ T-cell response in DR4-transgenic mice to a hybrid peptide linking the Ii-Key segment of the invariant chain to the melanoma gp100(48-58) MHC class II epitope," J Immunother., 28(4):352-358, Jul.-Aug. 2005.
Kallinteris et al., "Ii-Key/MHC class II epitope hybrid peptide vaccines for HIV," Vaccine, 21(27-30):4128-4132, Oct. 1, 2003.
Kallinteris et al., "Ii-Key/MHC class II epitope hybrids: a strategy that enhances MHC class II epitope loading to create more potent peptide vaccines," Expert Opin Biol Ther., 6(12):1311-1321, Dec. 2006.
Kallinteris et al., "Linkage of Ii-Key segment to gp100(46-58) epitope enhances the production of epitope-specific antibodies," Vaccine, 23(17-18):2336-2338, Mar. 18, 2005.
Lu et al., "Suppression of major histocompatibility complex class II-associated invariant chain enhances the potency of an HIV gp120 DNA vaccine," Immunology, 120(2): 207-216, Feb. 2007.

* cited by examiner

FR74      amino-KDISYLYRFNWNHCG-amide
FR74.1    acetyl-KDISYLYRFNWNHCG-amide
FR74.2    Acetyl-LRMK-ava-KDISYLYRFNWNHCG-amide
FR74.3    Acetyl-KDISYLYRFNWNHCG-RARR-FYPSYHSTPQRP-amide
FR74.4    Acetyl-LRMK-ava-KDISYLYRFNWNHCG-RARR-FYPSYHSTPQRP-amide

FIG. 2

Table 1: Nonconventional amino acid linkers

| Peptide name | Ii-Key and Linker | Antigen region |
|---|---|---|
| FR74.1 (Native) | None | ac-KDISYLYRFNWNHCG-amide |
| FR74.2 | ac-LMRK-(4)aminobutyric acid- | KDISYLYRFNWNHCG-amide |
| FR74.5 | ac-LMRK-(5)aminobutyric acid- | KDISYLYRFNWNHCG-amide |
| FR74.6 | ac-LMRK-(6)aminobutyric acid- | KDISYLYRFNWNHCG-amide |
| FR74.7 | ac-LMRK-(7)aminobutyric acid- | KDISYLYRFNWNHCG-amide | ac-acetate, LMRK=Ii-Key

FIG. 16

Table 2: Protease sensitive DC3 peptide linkers

| Peptide name | Antigenic region | Linker (bold) and DC3 |
|---|---|---|
| FR74.1 (Native) | ac-KDISYLYRFNWNHCG-amide | None |
| FR74.3 | ac-KDISYLYRFNWNHCG- | -RARR-FYPSYHSTPQRP-amide |
| FR74.8 | ac-KDISYLYRFNWNHCG- | -VRVV-FYPSYHSTPQRP-amide |
| FR74.9 | ac-KDISYLYRFNWNHCG- | -RRRR-FYPSYHSTPQRP-amide |
| FR74.10 | ac-KDISYLYRFNWNHCG- | -RKRR-FYPSYHSTPQRP-amide |
| FR74.11 | ac-KDISYLYRFNWNHCG- | -RARYKR-FYPSYHSTPQRP-amide | ac=acetate, A=alanine, R=arginine, K=lysine

FIG. 17

Table 3: DC3 peptide reduction

| Peptide name | Antigenic region | Linker (bold) and DC3 |
|---|---|---|
| FR74.1 (Native) | Biotin-KDISYLYRFNWNHCG- | None |
| FR74.3 | Biotin-KDISYLYRFNWNHCG- | -RARR-FYPSYHSTPQRP-amide |
| FR74.12 | Biotin-KDISYLYRFNWNHCG- | -RRRR-SYHSTPQRP-amide |
| FR74.13 | Biotin-KDISYLYRFNWNHCG- | -RRRR-STPQRP-amide |
| FR74.14 | Biotin-KDISYLYRFNWNHCG- | -RRRR-QRP-amide |

FIG. 18

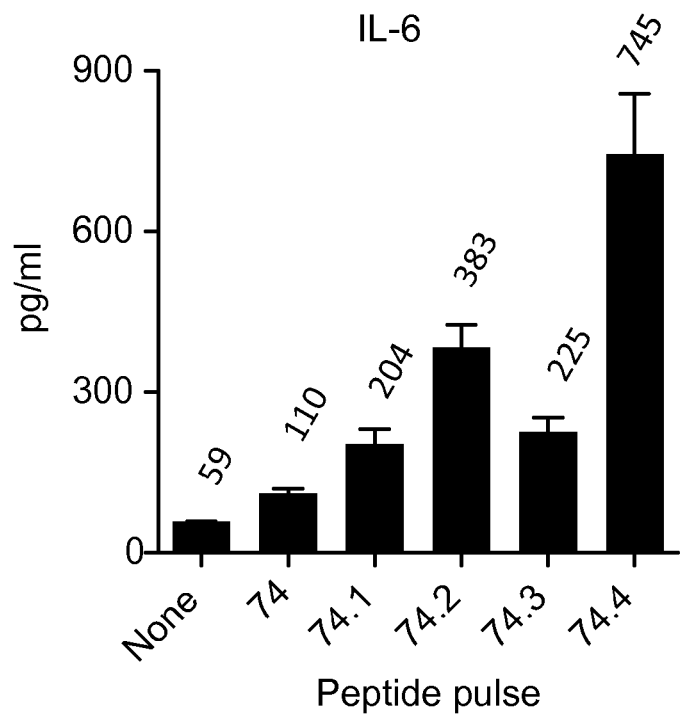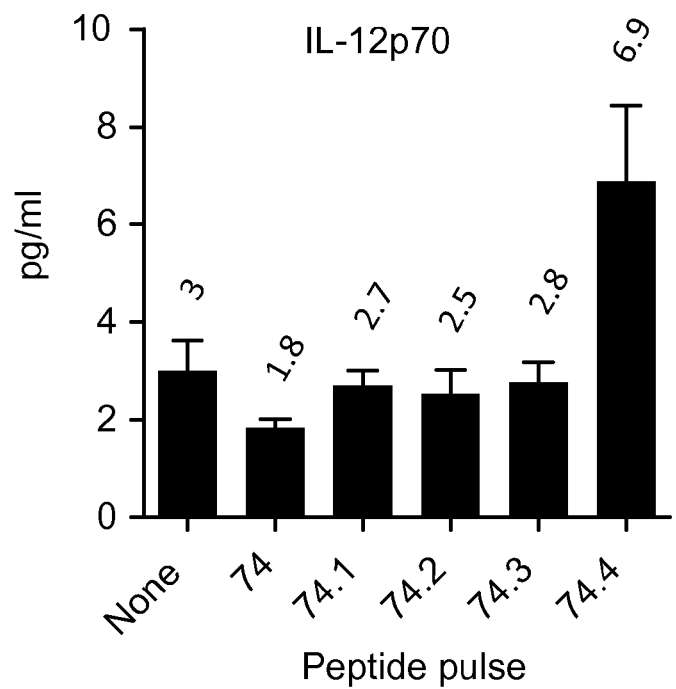
FIG. 24

METHODS AND MATERIALS FOR GENERATING T CELLS

CROSS-REFERENCE TO RELATED APPLICATIONS

This application is a National Stage application under 35 U.S.C. §371 and claims benefit under 35 U.S.C. §119(a) of International Application No. PCT/US2010/024792, having an International Filing Date of Feb. 19, 2010, which is claims the benefit of U.S. Provisional Application Ser. No. 61/153,771, filed Feb. 19, 2009. The disclosure of the prior applications are considered part of (and are incorporated by reference in) the disclosure of this application.

STATEMENT AS TO FEDERALLY SPONSORED RESEARCH

This invention was made with government support under grant numbers CA100764/CA015083 awarded by the National Institute of Health. The government has certain rights in the invention.

BACKGROUND

1. Technical Field

The document relates to methods and materials for generating T cells (e.g., antigen-specific CD4+ T cells). For example, this document relates to using nested MHC class II epitopes as vaccines to generate activated CD4+ T cells in vivo or as reagents to generate activated CD4+ T cells ex vivo.

2. Background Information

Adoptive transfer of large numbers of antigen-specific T cells has a therapeutic potential for being used to regress tumors or eliminate infection. Effective adoptive T cell therapy appears to require antigen-specificity as activated non-specific T cells do not appear to be very effective. The generation of antigen-specific T cells typically takes weeks to months and results in weak antigen-specific responses, T cell exhaustion, senescence, and loss of polyclonality. Strategies are being examined to improve antigen-specific T cell generation. One of the more often employed strategies is to supplement cell culture media with T cell activating cytokines that have recently been made available by better production capabilities. Another strategy used, although less easily employed, is the use of tetramers to isolate antigen-specific T cells for culture. Yet another is to immunize in vivo and harvest lymph node cells for eventual ex vivo expansion.

SUMMARY

This document provides methods and materials involved in generating T cells (e.g., antigen-specific CD4+ T cells). For example, this document provides methods and materials for using nested MHC class II epitopes to generate CD4+ T cells ex vivo. The nested MHC class II epitopes provided herein can include (a) an invariant chain (Ii) amino acid sequence, (b) an MHC class II epitope, and (c) a DC3 amino acid sequence. In some cases, a linker amino acid sequence can be located between the Ii amino acid sequence and the MHC class II epitope. In some cases, a protease cleavage site amino acid sequence can be located between the MHC class II epitope and the DC3 amino acid sequence. Such nested MHC class II epitopes can be used to create large pools of antigen-specific CD4+ T cells in an ex vivo manner.

In general, one aspect of this document features a polypeptide comprising, or consisting essentially of, an invariant chain amino acid sequence, an MHC class II epitope amino acid sequence, and a DC3 amino acid sequence. The polypeptide is between 20 and 80 amino acids in length. The invariant chain amino acid sequence can comprise LMRK (SEQ ID NO:3). The MHC class II epitope amino acid sequence can comprise KDISYLYRFNWNHCG (SEQ ID NO:1). The DC3 amino acid sequence can comprise FYPSYHSTPQRP (SEQ ID NO:2).

In another aspect, this document features a method for activating T cells in a mammal. The method comprises, or consists essentially of, administering a composition comprising a polypeptide to the mammal, wherein the polypeptide comprises an invariant chain amino acid sequence, an MHC class II epitope amino acid sequence, and a DC3 amino acid sequence, wherein the polypeptide is between 20 and 80 amino acids in length. The invariant chain amino acid sequence can comprise LMRK (SEQ ID NO:3). The MHC class II epitope amino acid sequence can comprise KDISYLYRFNWNHCG (SEQ ID NO:1). The DC3 amino acid sequence can comprise FYPSYHSTPQRP (SEQ ID NO:2). The composition can comprise a plurality of different polypeptides, wherein each of the plurality of different polypeptides comprises the invariant chain amino acid sequence, the MHC class II epitope amino acid sequence, and the DC3 amino acid sequence, and is between 20 and 80 amino acids in length. Each of the plurality of different polypeptides can comprise a different MHC class II epitope amino acid sequence.

In another aspect, this document features a method for obtaining activated T cells. The method comprises, or consists essentially of, contacting T cells with a polypeptide in an ex vivo manner, wherein the polypeptide comprises an invariant chain amino acid sequence, an MHC class II epitope amino acid sequence, and a DC3 amino acid sequence, wherein the polypeptide is between 20 and 80 amino acids in length. The invariant chain amino acid sequence can comprise LMRK (SEQ ID NO:3). The MHC class II epitope amino acid sequence can comprise KDISYLYRFNWNHCG (SEQ ID NO:1). The DC3 amino acid sequence can comprise FYPSYHSTPQRP (SEQ ID NO:2).

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 2 depicts the amino acid sequences of exemplary polypeptides (FR7, SEQ ID NO:1; FR74.1, SEQ ID NO:1; FR74.2, SEQ ID NO:5; FR74.3, SEQ ID NO:6; and FR74.4, SEQ ID NO:7). FR74 includes the native polypeptide sequence (SEQ ID NO:1). Ava=ε-amino-n-valeric acid. The CD4 T cell epitope is single underlined. The Ii-key motif is double underlined (SEQ ID NO:44), and the DC3 motif (SEQ ID NO:2) is boxed. RARR (SEQ ID NO:4) is the furin sensitive linker.

FIG. 16 contains a table of nonconventional amino acid linkers. The KDISYLYRFNWNHCG amino acid sequence is set forth in SEQ ID NO:1.

FIG. 17 contains a table of protease sensitive amino acid linkers (FR74.1, SEQ ID NO:1; FR74.3, SEQ ID NO:6; FR74.8, SEQ ID NO:8; FR74.9, SEQ ID NO:9; FR74.10, SEQ ID NO:10; and FR74.11, SEQ ID NO:11).

FIG. 18 contains a table of DC3 reduced polypeptides (FR74.1, SEQ ID NO:1; FR74.3, SEQ ID NO:13; FR74.12, SEQ ID NO:14; FR74.13, SEQ ID NO:15; and FR74.14, SEQ ID NO:16).

FIG. 24. Modified polypeptides induce different release of IL-6 and IL-12p70. Shown are the concentrations of IL-6 and IL-12p70 within DC culture media 48 hours after pulsing with the indicated polypeptides. Each bar is the mean (±s.e.m.) of duplicate samples. A repeat experiment yielded similar results. Values associate with each bar are the actual mean concentrations measured.

DETAILED DESCRIPTION

Figure 1:
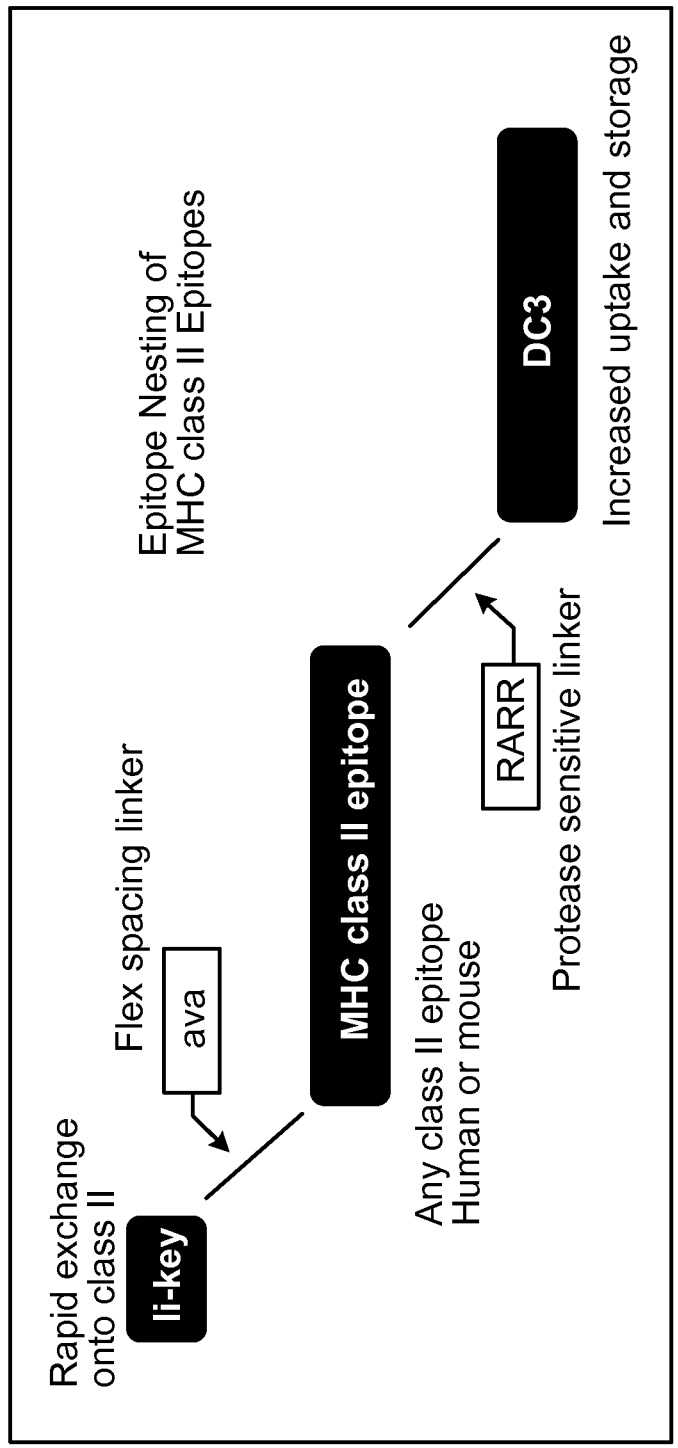
FIG. 1 is a schematic of an example epitope nesting model that can be used for ex vivo expansion.

This document provides methods and materials involved in generating T cells (e.g., antigen-specific CD4+ T cells). For example, this document provides methods and materials for using nested MHC class II epitopes to generate CD4+ T cells ex vivo. The nested MHC class II epitopes provided herein can be a polypeptide that includes (a) an invariant chain (Ii) amino acid sequence, (b) an MHC class II epitope, and (c) a DC3 amino acid sequence (FIG. 1). An invariant chain (Ii) amino acid sequence can be LMRK (SEQ ID NO:3), LRMKLPKS (SEQ ID NO:17), LRMKLPKSAKP (SEQ ID NO:18), or LRMKLPKSAKPVSK (SEQ ID NO:19). Any type of MHC class II epitope can be incorporated into a polypeptide provided herein to create a nested MHC class II epitope. Examples include, without limitation, MHC class II epitopes from FRα polypeptides (e.g., KDISYLYRFNWN-HCG (SEQ ID NO:1)), CEA polypeptides (e.g., LLTFWN-PPTTAKLTI (SEQ ID NO:20), YLWWVNNQSLPVSPR (SEQ ID NO:21), RTTVKTITVSAELPK (SEQ ID NO:22), and YACFVSNLATGRNNS (SEQ ID NO:23)), HER-2/neu polypeptides (e.g., NLELTYLPTNASLSF (SEQ ID NO:24), HNQVRQVPLQRLRIV (SEQ ID NO:25), LSVFQN-LQVIRGRIL (SEQ ID NO:26), and PIKWMALESILRRRF (SEQ ID NO:27)), or IGFBP-2 polypeptides (e.g., LLPLL-PLLLLLLGAS (SEQ ID NO:28), PLLLLLLGASGGGGG (SEQ ID NO:29), ERGPLEHLYSLHIPN (SEQ ID NO:30), and TGKLIQGAPTIRGDP (SEQ ID NO:31)). A DC3 amino acid sequence can be FYPSYHSTPQRP (SEQ ID NO:2).

In some cases, a linker amino acid sequence can be located between the Ii amino acid sequence and the MHC class II epitope. Examples of appropriate linker sequences include, without limitation, AVA sequences and (GGSGGS)n sequences, where n is 1 or more than 1 (e.g., 2, 3, 4, 5, or 6 (SEQ ID NOs:34-39, respectively)). The GGSGGS (SEQ ID NO:32) amino acid sequence is set forth in SEQ ID NO:32. In some cases, a protease cleavage site amino acid sequence can be located between the MHC class II epitope and the DC3 amino acid sequence. Examples of appropriate protease cleavage site amino acid sequences include, without limitation, RARR (SEQ ID NO:4) and any other R-X-(R/K)-R (SEQ ID NO:40) furin consensus cleavage site.

The polypeptides provided herein, which contain a nested MHC class II epitope, can be between about 20 amino acids and about 100 amino acids in length (e.g., about 20 to about 90 amino acids in length, about 20 to about 80 amino acids in length, about 20 to about 70 amino acids in length, about 20 to about 60 amino acids in length, about 20 to about 50 amino acids in length, about 30 to about 100 amino acids in length, about 40 to about 100 amino acids in length, about 50 to about 100 amino acids in length, about 60 to about 100 amino acids in length, about 70 to about 100 amino acids in length, about 25 to about 60 amino acids in length, about 30 to about 55 amino acids in length, or about 32 to about 54 amino acids in length).

The polypeptides provided herein can be substantially pure. The term "substantially pure" with respect to a polypeptide refers to a polypeptide that has been separated from cellular components with which it is naturally accompanied. For example, a synthetically generated polypeptide can be a substantially pure polypeptide. Typically, a polypeptide provided herein is substantially pure when it is at least 60 percent (e.g., 65, 70, 75, 80, 90, 95, or 99 percent), by weight, free from proteins and naturally-occurring organic molecules with which it is naturally associated. In general, a substantially pure polypeptide will yield a single major band on a non-reducing polyacrylamide gel.

The polypeptides provided herein can be prepared in a wide variety of ways. Because of their relatively short size, the polypeptides can be synthesized in solution or on a solid automatic synthesizer in accordance with known protocols. See, for example, Stewart and Young, *Solid Phase Polypeptide Synthesis*, 2d. ed., Pierce Chemical Co. (1984); Tam et al., *J. Am. Chem. Soc.*, 105:6442 (1983); Merrifield, *The Polypeptides*, Gross and Meienhofer, ed., academic Press, New York, pp. 1-284 (1979).

In some cases, recombinant DNA technology can be used wherein a nucleotide sequence which encodes a polypeptide provided herein is inserted into an expression vector, introduced (e.g., by transformation or transfection) into an appropriate host cell, and cultivated under conditions suitable for expression. These procedures are generally known in the art, as described generally in Sambrook et al., *Molecular Cloning, A Laboratory Manual*, Cold Spring Harbor Press, Cold Spring Harbor, N.Y. (1982), and Ausubel et al., (ed.) *Current Protocols in Molecular Biology*, John Wiley and Sons, Inc., New York (1987), and U.S. Pat. Nos. 4,237,224; 4,273,875; 4,431,739; 4,363,877; and 4,428,941, for example.

The polypeptides provided herein can be incubated with a population of T cells to generate an activated pool of CD4+ T cells that can be specific for the epitope present within the polypeptide used. For example, the polypeptides provided herein can be used in an ex vivo manner to created antigen-specific CD4+ T cells that can be used to treat cancers or infections (e.g., bacterial, viral, or parasitic infections). In some cases, the polypeptides provided herein can be used to generate a pool of activated antigen-specific CD4+ T cells that can be used alone, or in combination with monoclonal antibody therapy, CTL therapy, or both monoclonal antibody therapy and CTL therapy, to treat cancer or an infection. For example, an anti-folate receptor-specific monoclonal antibody therapy can be combined with infusion of folate-specific CD4 T cells or combination infusion of either folate receptor alpha-specific CD4 T cells and CD8 T cells, or a combination of the three.

The invention will be further described in the following examples, which do not limit the scope of the invention described in the claims.

EXAMPLES

Example 1

Epitope Nesting Results in Augmented Numbers of High Avidity Antigen-Specific Th Cells Folate Receptor Alpha Polypeptide A native helper epitope designated FR74 was a peptide derived from the folate receptor alpha (FRα) (FIG. 2). FRα (also referred to as folate binding protein) is a glycophosphatidyl-anchored membrane glycoprotein that mediates cellular uptake of folate. This polypeptide is over-expressed on many cancers at levels of up to 80-90-fold relative to the levels observed on normal tissues. FRα is an antigen that can be used across strains, which allows one to test various strategies amongst many different I-A and I-E backgrounds. FR74 (See shaded region of FIG. 2) was chosen because it is highly immunogenic when used as a vaccine with complete Freund's adjuvant (CFA), CpG, or GM-CSF, but is relatively non-immunogenic when used to generate T cell lines using activated DC. FR74 was modified at the amino-terminus end with an Ii-key and at the carboxy terminus with a DC3 amino acid motif (FIG. 2). To reduce enzymatic degradation in cell culture, the amino terminus of FR74 was acetylated to make FR74.1. FR74.2 is FR74 conjugated to Ii-key. It is attached with a flexible, noncleavable linker FR74.3 is FR74 conjugated to a DC3 polypeptide using a furin sensitive linker to permit cleavage. Furin is an endopeptidase that normally proteolytically activates a large number of proproteins in the cell, and it is predominantly localized to the endosomal system (Thomas, G., Nat. Rev. Mol. Cell Biol., 3(10):753-66 (2002)). FR74.4 is a dual conjugated polypeptide. All modified peptides were acetylated at the amino terminus to prevent degradation.

Figure 3A:
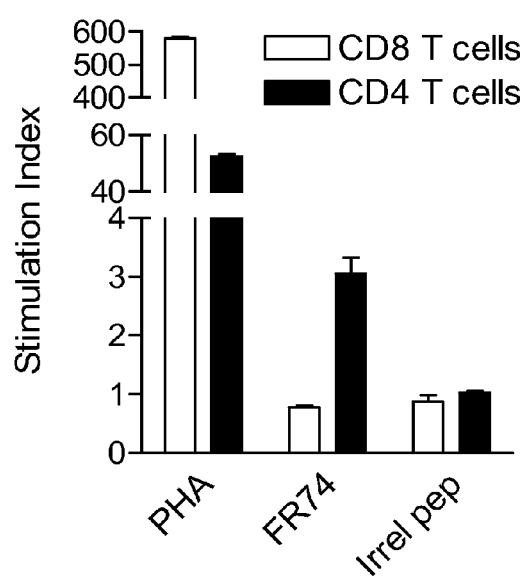
FIG. 3A is a plotting the stimulation indices from a proliferation assay in which CD4 and CD8 T cells from FR74-immunized mice were tested for response to non-specific stimulation (PHA), FR74 polypeptide, or an irrelevant polypeptide (Irrel pep). The stimulation index is the ratio of the thymidine incorporation in the sample with antigen and the controls ample.

The FR74 polypeptide can activate CD4 T cells in FVB and B6 mice, and it is naturally processed. CD4 T cells, but not CD8 T cells, derived from FR74-immunized FVB mice responded with increased proliferation to the FR74 polypeptide (FIG. 3A).

Figure 3B:
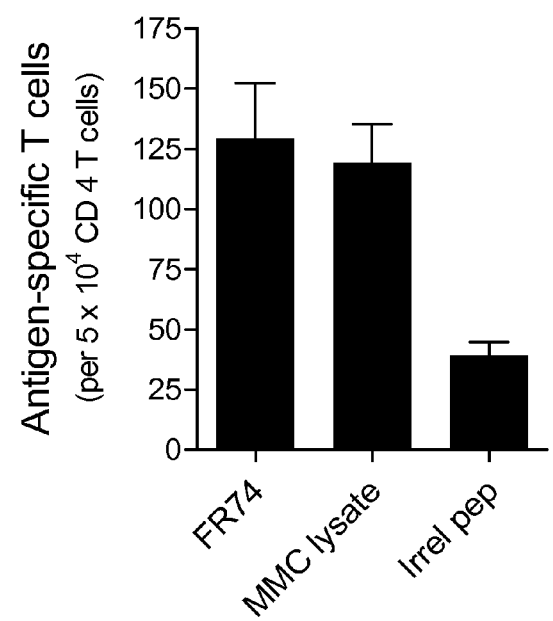
FIG. 3B is a graph plotting results of an IFN-γ ELIspot (enzyme-linked immunosorbent spot) analysis of FR74-specific T cell lines stimulated in vitro with dendritic cells (DC) pulsed with either FR74 polypeptide, FRα-overexpressing tumor cell lysate (MMC lysate), or an irrelevant polypeptide antigen (Irrel pep). Each bar is the mean (±s.e.m.) of 3 replicates.

Furthermore, FR74-specific T cell lines recognize FRα+ tumor lysates (MMC, a tumor cell line derived from a spontaneous tumor from the FVB/N based neu transgenic mouse) pulsed onto DC (FIG. 3B).

Figure 4:
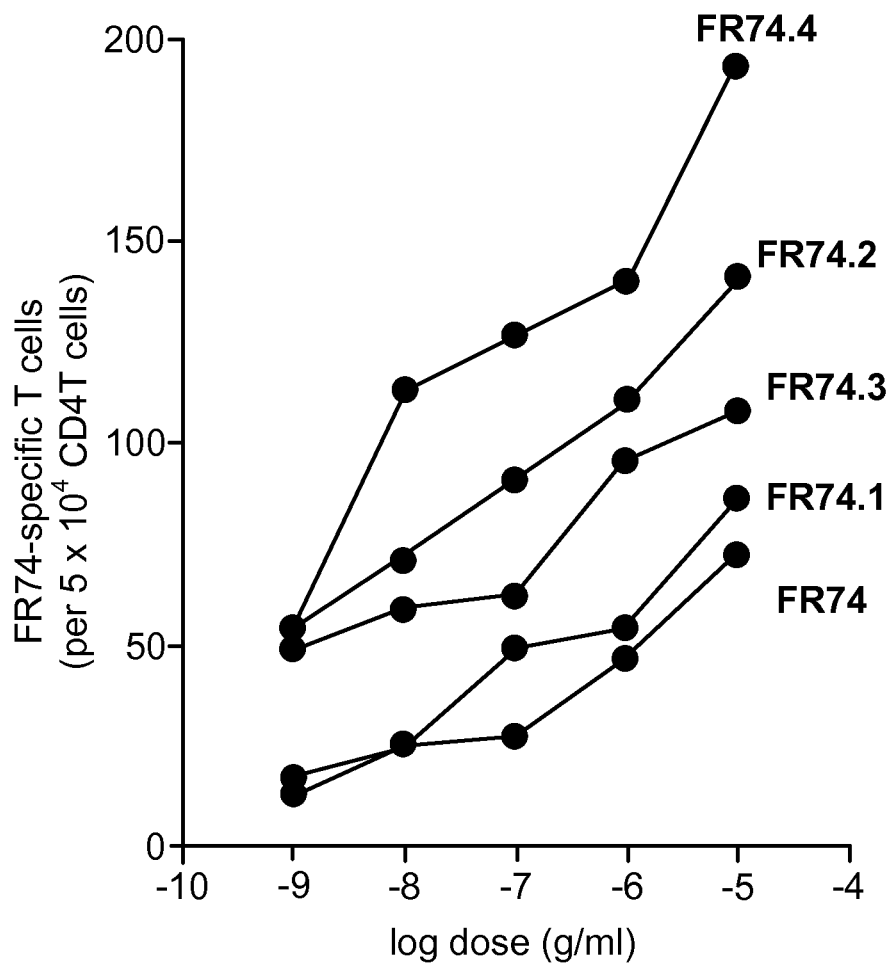
FIG. 4 is a graph plotting the results an IFN-γ ELIspot analyses of T cell cultures incubated with the indicated polypeptides. Epitope nesting greatly augments the numbers of antigen-specific T cells. T cells were tested in ELIspot against native FR74 polypeptide at various concentrations. Each data point is the mean of 3 determinations.
Figure 5:
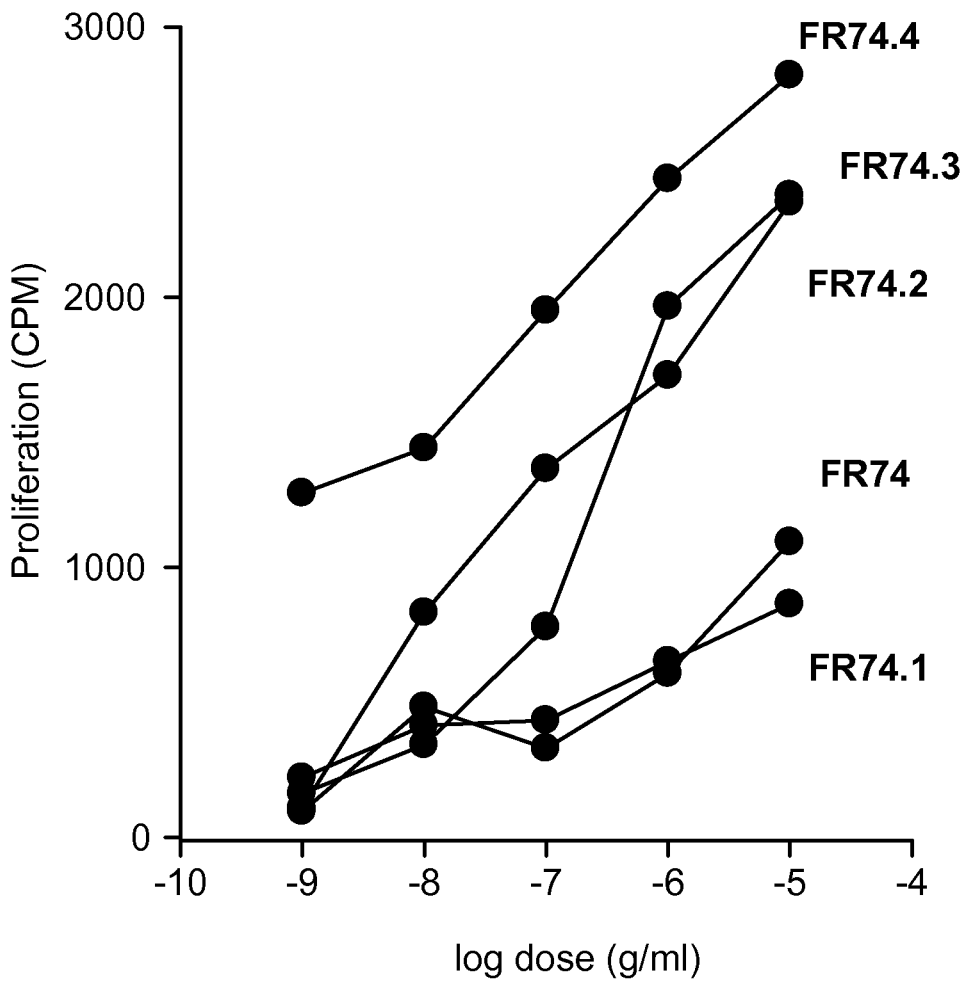
FIG. 5 is a graph plotting proliferation (as measured by thymidine incorporation (CPM)) of T cells treated with the indicated polypeptides. Epitope nesting activates high affinity antigen-specific T cells. T cells were tested for incorporation against native FR74 polypeptide at various concentrations. Each data point is the mean of 3 determinations.
Figure 6:
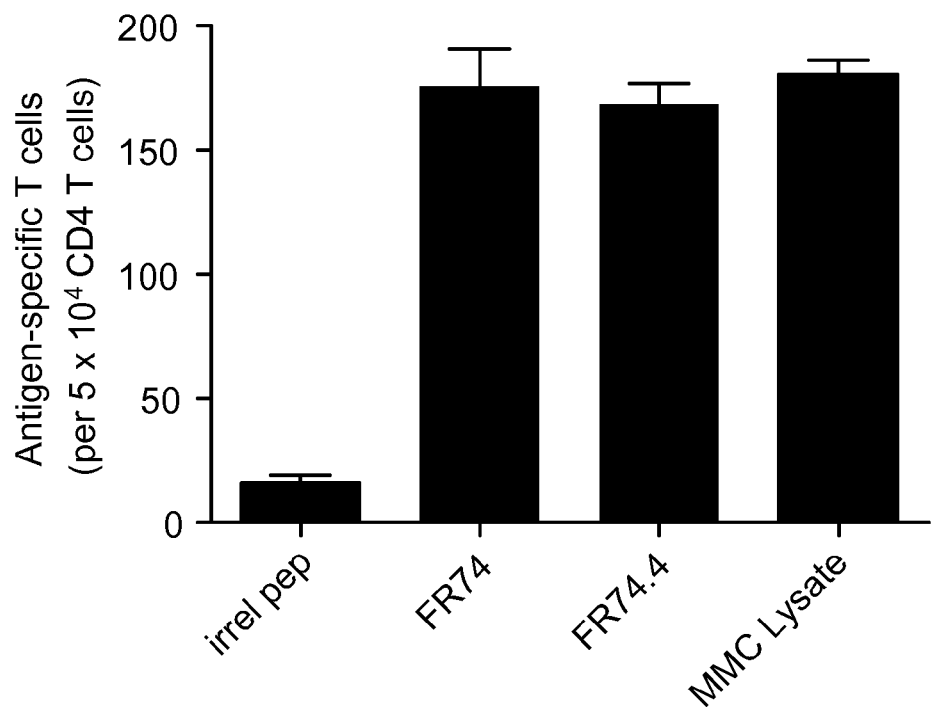
FIG. 6. FR74-specific T cells generated with modified polypeptides recognized tumor lysates. Graph shows the results of an IFN-γ ELIspot assay assessing the response of T cells to native FR74 polypeptide, culture polypeptide FR74.4, and irrelevant polypeptide (irrel pep), and DC pulsed with lysates of tumor cells overexpressing FRα. Each bar is the mean (±s.e.m.) of 3 replicates.

Epitope Nesting Results in Enhanced Ex Vivo Activation of Antigen-Specific T Cells Both the Ii-key and DC3 single modifications resulted in greatly enhanced FR74-specific T cells within 12 days of culture as compared to the controls (FIG. 4). Notably, nesting of FR74 between the two polypeptides resulted in the generation of high avidity T cells capable of responding at concentrations of peptides as low as $10^{-9}$ g/mL (FIG. 4). Modification of FR74 with both DC3 and Ii-key resulted in T cell reactivity greater than either modification alone. Both modifications resulted in an additive or potentially synergistic effect with each other, suggesting interacting but non-overlapping mechanisms of T cell generation. In terms of proliferation, only the dual modified polypeptide was able to generate T cells that were able to proliferate at $10^{-9}$ g/mL (FIG. 5). In other studies, FR74-specificity was observed to be fully maintained after ex vivo expansion with anti-CD3/CD28 magnetic beads, thus demonstrating that the approach can be scaled-up and robust enough for FDA approval. Additional evidence demonstrated that the T cells generated with the dual modified polypeptides retain the capability to respond to naturally processed antigen, in the form of DC pulsed with FRα-expressing tumor cells (FIG. 6).

Figure 7:
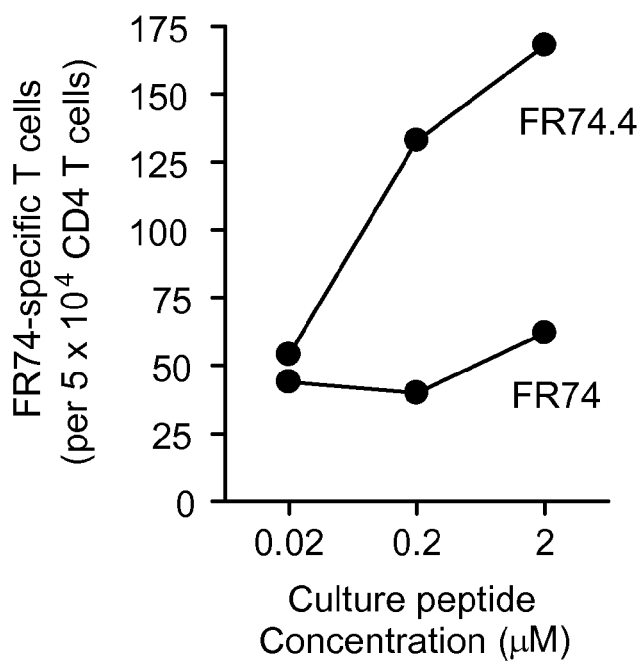
FIG. 7. FR74.4 is superior to native polypeptide under conditions of equal molarity. Graph shows the results of an IFN-γ ELIspot assay assessing the response of either FR74.4 or FR74-specific T cell cultures to native FR74 polypeptide. The T cells were generated at varying concentrations of polypeptides (x-axis). Each point is the mean (±s.e.m.) of 3 replicates.

The comparisons devised above use polypeptides that are of differing masses. So as to avoid problems related to these differences, the experiments were performed using equal masses of polypeptide. Since this introduces differences (albeit, minor) in the molarity of the MHC class II epitope, we also examined whether there were differences in the T cell reactivity when T cells were incubated under equal molar amounts of polypeptides. As shown in FIG. 7, FR74.4 exhibited superior ex vivo generation of FR74-specific T cells relative to the native polypeptide. Thus, regardless of equal molarity or mass, modification resulted in superior T cell generation.

Figure 8A:
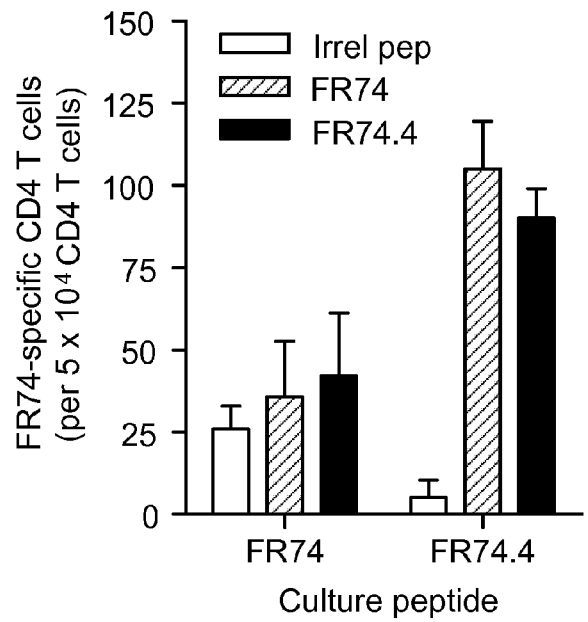
FIG. 8. Tumor antigen-specific T cells can be elicited from native pools. Panel A shows the results of IFN-gamma ELIspot analysis of FR74- and FR74.4-stimulated native T cells. Each culture was assayed for reactivity toward FR74, FR74.4, an irrelevant (irrel) polypeptide, or media. Each data point is the mean of 3 replicates. Panel B shows flow cytometry dot plots demonstrating high purity of naïve T cell populations.
Figure 8B:
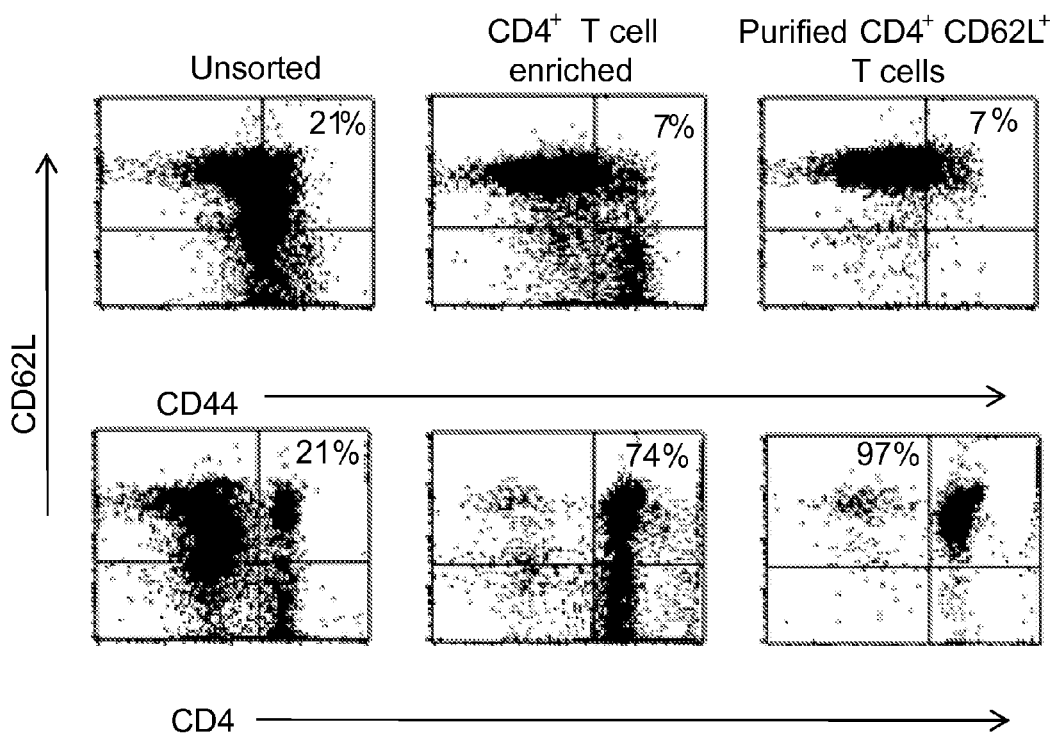

The capability of the nested epitopes to elicit antigen-specific T cells from naïve pools was tested. Remarkably, as shown in FIG. 8, the results demonstrate that nesting results in the generation of antigen-specific T cells from naïve pools of T cells while no specific reactivity was elicited with the native epitopes.

Figure 9A:
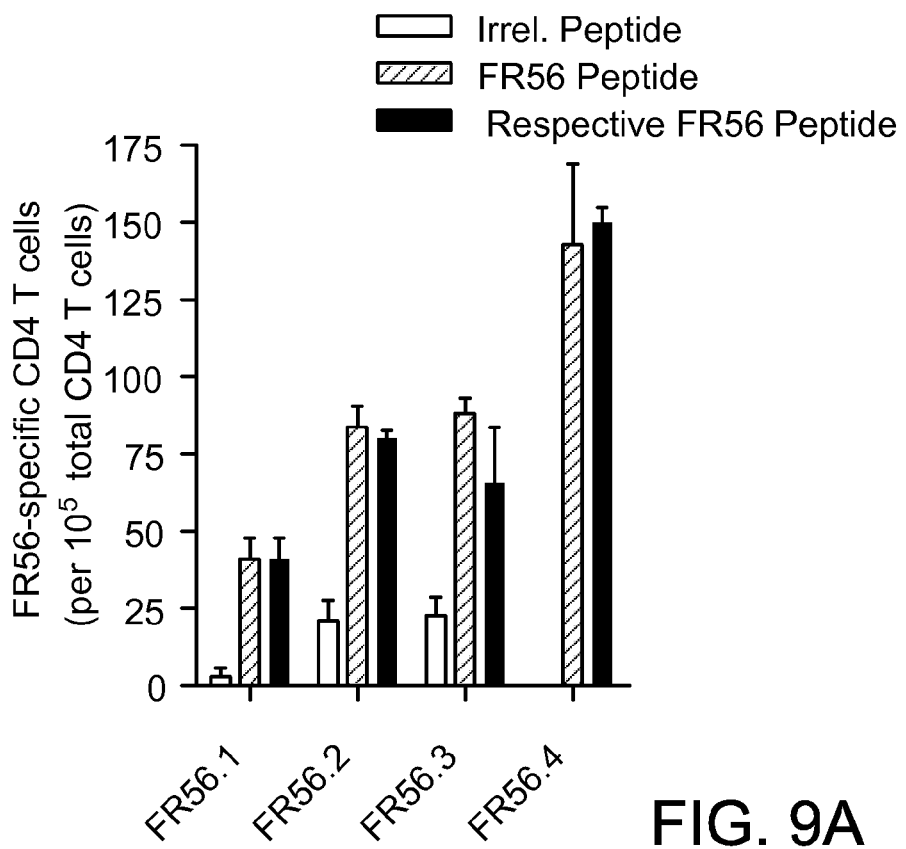
FIG. 9. Effects of polypeptide modifications are independent of core MHC class II peptide and species indifferent. Panels A and B show IFN-γ ELIspot and proliferation results, respectively, of human T cell lines generated against a human FRα-derived polypeptide. Each bar is the mean (±s.e.m.) of 3 replicates. Panel C: Proliferation responses of FR74-specific T cells line generated in B6 (I-Ab) using FR74 or FR74.4 polypeptides (mean±SE, n=2). Panel B: IFN-γ ELIspot results of OVA323-specific CD4 T cell lines generated with either OVA323 or OVA323.4 (mean±SE, n=3).
Figure 9B:
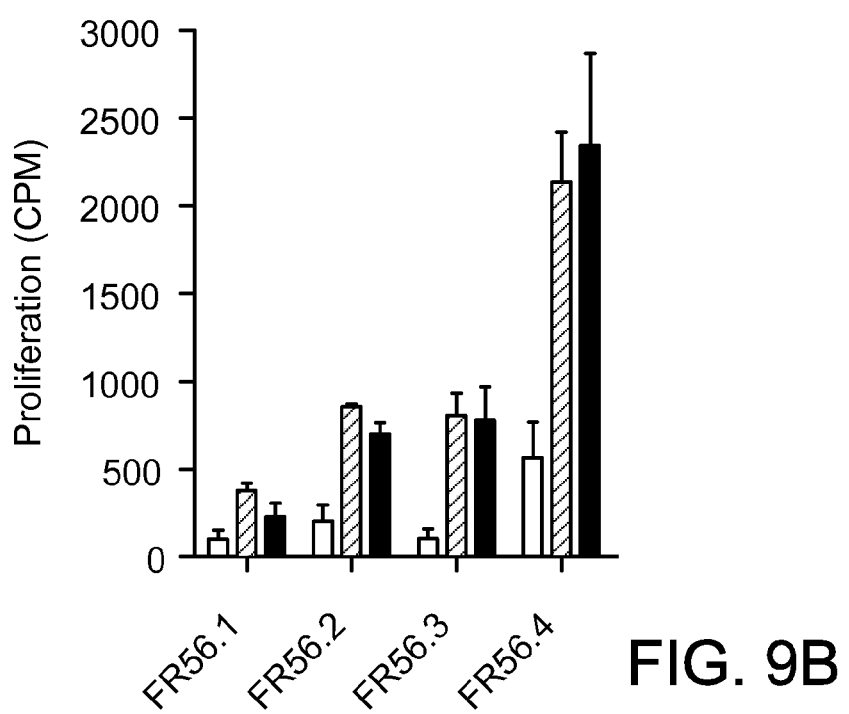
Figure 9C:
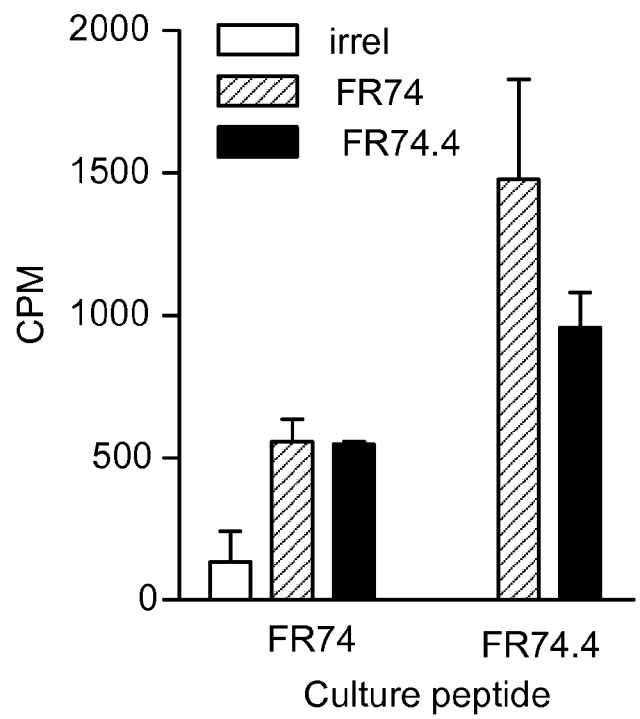
Figure 9D:
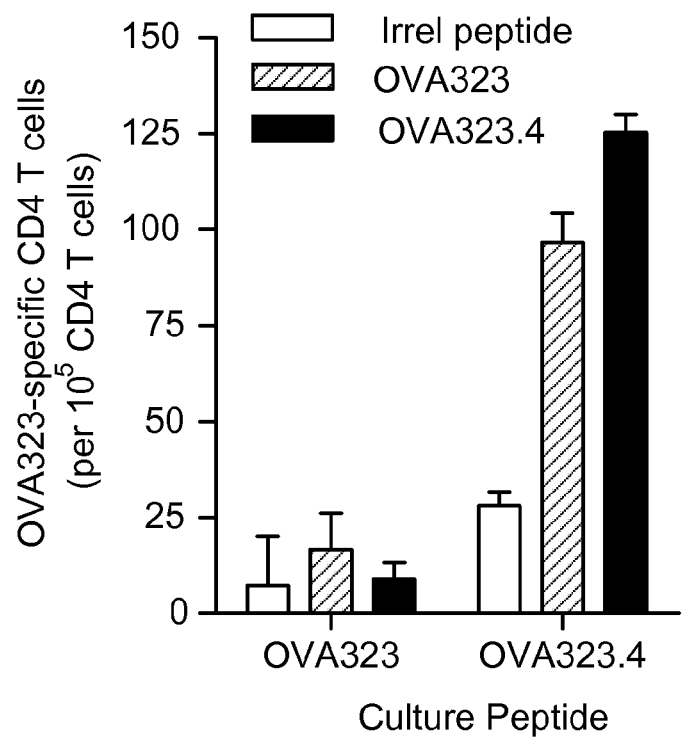

Ex Vivo Activation Mediated by Epitope Nesting does not Depend on Either the Sequence of the MHC Class II Peptide or the Species The following was performed to determine whether nesting of a human epitope would yield similar results. For this, the FR56 polypeptide derived from human FRα was chosen (Knutson et al., *J. Clin. Onc.*, 24:4254-4261 (2006)). The sequence of this polypeptide was QCRPWRKNACCSTNT (SEQ ID NO:33). FR56 was modified identically to the murine FR74 polypeptide as described herein using the 0.1, 0.2, 0.3, and 0.4 nomenclature. Monocyte-derived dendritic cells (DC) were prepared from the peripheral blood mononuclear of a normal healthy individual and pulsed with the modified polypeptides, FR56.1, FR56.2, FR56.3, or FR56.4. Purified CD4 T cells were added to the DC, and antigen-specific T cells were expanded for 12 days. At the end of the incubation period, the cells were assessed by IFN-γ ELIspot and proliferation analysis. The modifications behaved similarly with human cells and thus, the approach is neither epitope-specific nor species-specific (FIGS. 9A and 9B).

Figure 10:
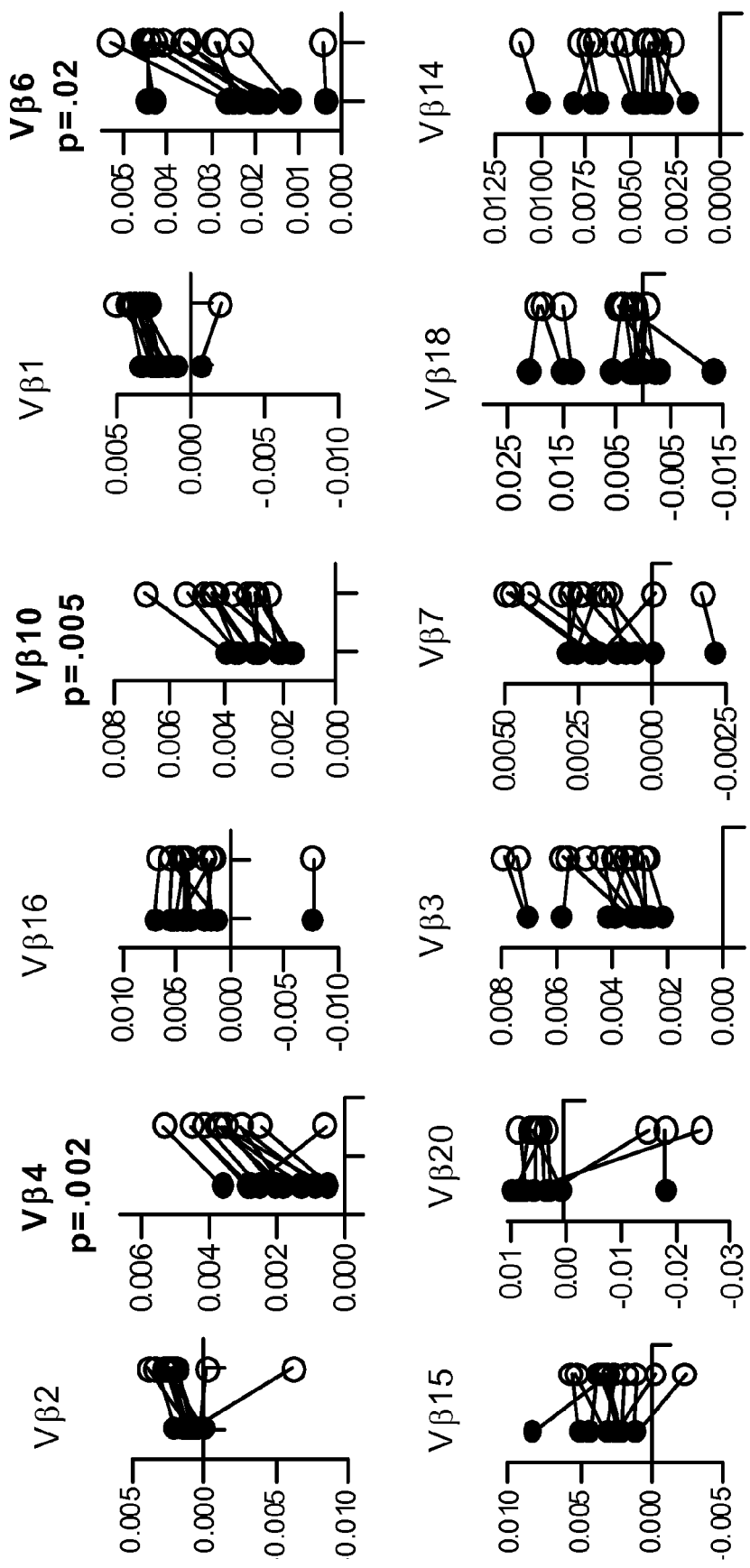
FIG. 10. Panel shows comparisons in the Vβ usage, respectively, of FR74 (closed symbols) and FR74.4 (open symbols) generated cultures. Changes are calculated from levels in CD4 T cells cultured in the absence of peptides and the x-axis of each plot represents baseline TCR usage in naïve CD4 T cells. Values above or below the axis show higher or lower usage levels relative to naïve T cells, respectively. P values were calculated using a paired T test. Each data point is a unique Vβ and Jβ pair.

Ex Vivo Activation Mediated by Nested Epitopes Involves the Recruitment of Specific TCR Vβ and Jβ Isoforms The ability of the nested MHC class II epitope-containing polypeptide to recruit specific TCRs was assessed using real-time PCR analysis as described elsewhere (Wettstein et al., *Nucleic Acid Res.*, 36(21):e140 (2008)). The nested PCR approach permitted the assessment of TCR usage of both Vβ and Jβ in a 96 well format and covered all murine TCRs. In brief, purified CD4 T cells were exposed to DC pulsed with either native FR74 or with FR74.4 followed by a 14 day incubation. RNA was extracted from each sample, including a baseline naïve CD4 T cell population, and subjected to PCR analysis. The outcome of a representative experiment is set forth in FIG. 10. The Vβ regions were listed in order of their appearance on the chromosome. FVB/N mice do not contain a copy of the Vβ5, Vβ8, or Vβ12 isoforms. In summary, it was found that of the Vβ's, epitope nesting preferentially used Vβ2, Vβ4, Vβ10, Vβ1, Vβ6, and Vβ3. Of the Jβ's, there was a preferential use of Jβ1.6, Jβ2.2, Jβ2.3, and Jβ2.7. These results strongly suggest that epitope nesting refines or focuses TCR usage. One key strength with using this approach is that one can identify specific TCR usage, and with the availability of antibodies to TCRs, it is possible to purify T cells with defined TCRs prior to ex vivo expansion.

Epitope Nesting Results in Enhanced Antigen Presentation and T Cell Activating Properties of DC In addition to focusing on the capabilities of the polypeptide modifications to enhance the generation of antigen-specific T cells, the mechanisms used by the modifications to enhance T cell generation, specifically focusing on the DC, were explored. The following results demonstrate that the biology of the DC in addition to antigen presentation is modified by the epitope nesting.

Figure 11:
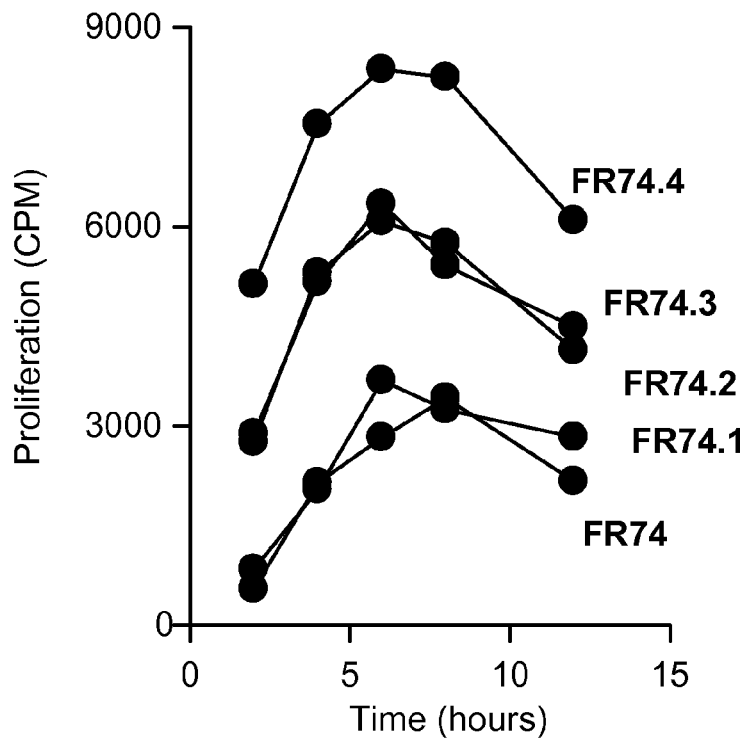
FIG. 11. DC pulse with nested epitopes are more immunogenic for longer period of time. Panel shows proliferation of a FR74-specific T cells line in response to DC pulsed with polypeptides shown over a time course of 2-12 hours.

Dendritic Cells Pulsed with Nested Epitopes Activate T Cells with Enhanced Efficacy for Longer Periods of Time Given the increased ability of the DC to generate antigen-specific T cells, it is possible that the DC are presenting higher levels of antigens for extended periods of time. In the absence of an antibody that recognizes the I-A$^q$:FR74-specific complex, this can be a difficult question to answer. However, the following experiment was designed that strongly supports that contention. In this experiment, DC were pulsed with equal masses of polypeptide for two hours followed by washing away the free polypeptide. The DC were then aged for varying periods of time, up to 12 hours followed by exposure to an FR74-specific T cell line to assess for proliferation. As was observed with the T cell response, each of the single modifications resulted in an increase immunogenicity of the DC (FIG. 11). Again, combining the polypeptide modifications led to an additive response (FIG. 11). These results demonstrate that the modified polypeptides increase the immunogenicity of the DC.

Figure 12:
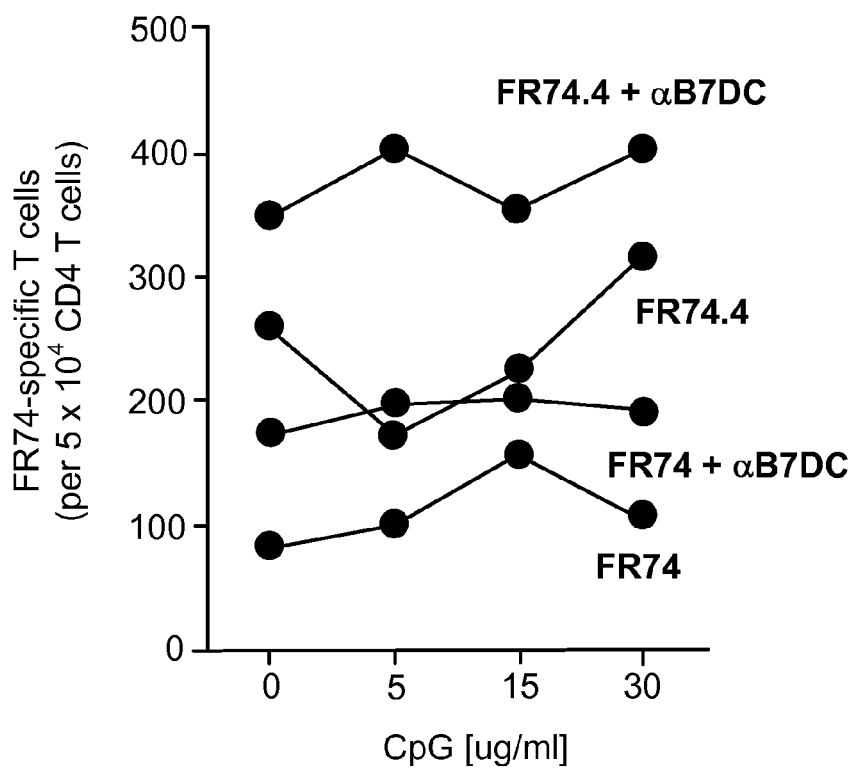
FIG. 12. B7-DC crosslinking enhances T cell responses. Panel shows IFN-γ ELIspot results of T cell cultures using DC pulsed with FR74.4 or FR74 in the presence or absence of B7-DC crosslinking antibody. Each data point is the mean (±s.e.m.) of 3 replicates.

DC Activation with B7-DC Crosslinking Antibody Results in Better Recruitment of Antigen-Specific T Cells with Epitope Nesting Others have recently shown in a series of publications that cross-linking of B7-DC on DC increases the antigen uptake capability of the DC while maintaining the mature T cell activating phenotype (Radhakrishnan et al., *Proc. Natl. Acad. Sci. USA*, 102(32):11438-43 (2005)). The following was performed to examine whether this could further improve the effects of epitope nesting. While the polypeptide modifications were effective alone, B7-DC crosslinking greatly facilitated T cell activation (FIG. 12). Thus, B7-DC crosslinking can be incorporated into an activation protocol.

Enhanced Presentation is not Due to Increased Levels of MHC Class or Co-Stimulatory, or Decreased Levels of CTLA-4

Figure 13:
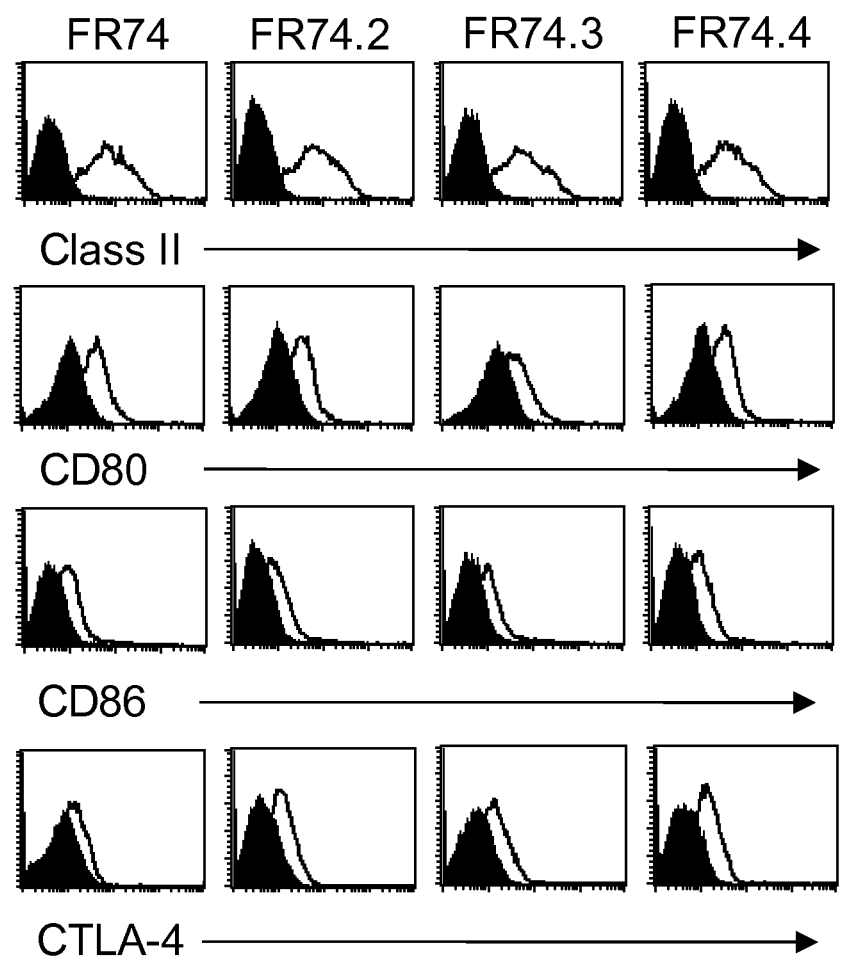
FIG. 13. Polypeptide modifications do not alter levels of Class II, co-stimulatory, or coinhibitory molecules. Panel shows flow cytometry of DC pulsed with FR74 or modified polypeptides for 4 hours. Filled histogram is the isotype control. Open histogram is the specific staining antibody signal.

One potential explanation for the enhanced T cell response to the nested epitopes is simply that the DC expresses more MHC class II molecules or other co-stimulatory molecules. This was examined for all of the polypeptides, except FR74.1, which is not different from FR74 and is shown in FIG. 13. The results reveal clearly and consistently no observable changes and suggest mechanisms other than upregulation or downregulation of these molecules that are important for the effects of epitope nesting.

Epitope Nesting Augments DC Secretion of Chemokines and Cytokines

Figure 14:
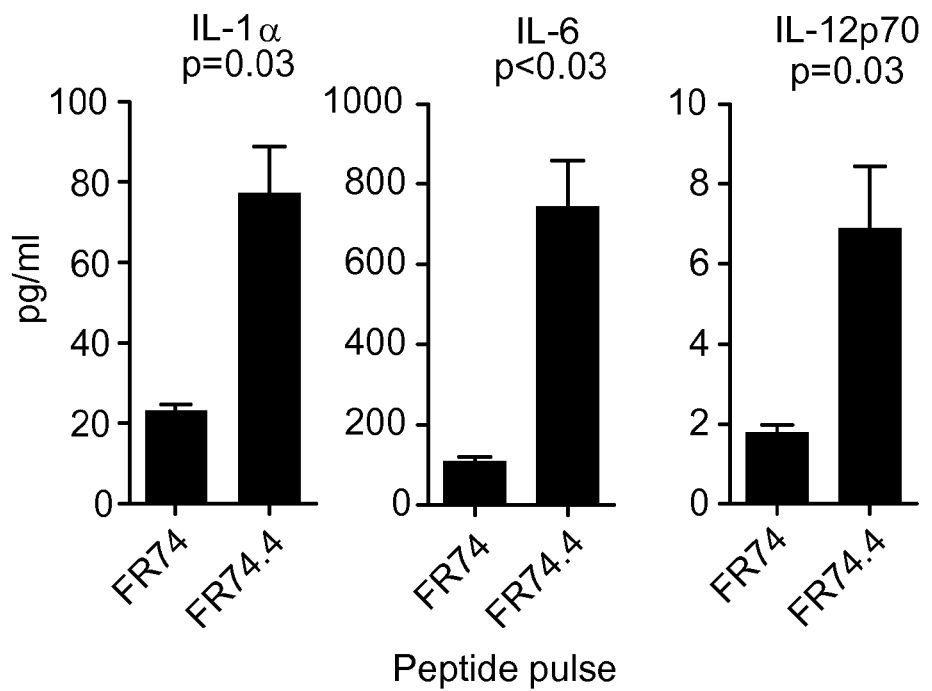
FIG. 14. DC pulsed with nested epitopes demonstrate higher cytokine secretion. Shown are the concentrations of cytokines within DC culture media 48 hours after pulsing with the indicated polypeptides. Each bar is the mean (±s.e.m.) of duplicates samples. A repeat experiment yielded similar results.
Figure 15:
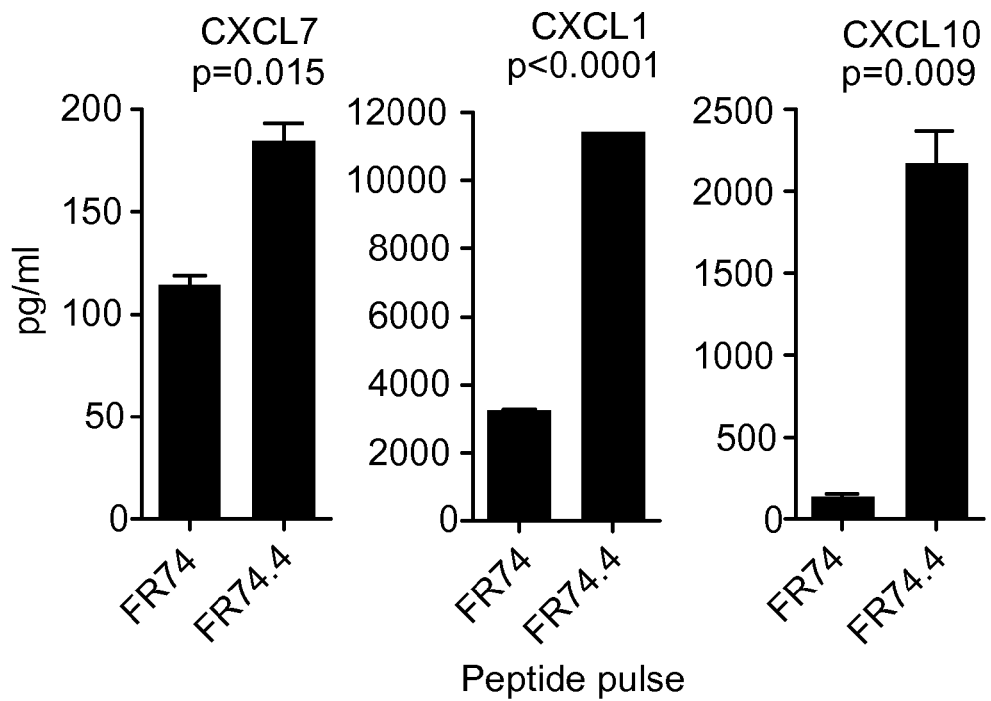
FIG. 15. DC pulsed with nested epitopes demonstrate higher chemokine secretion. Shown are the concentrations of chemokines within DC culture media 48 hours after pulsing with the indicated polypeptides. Each bar is the mean (±s.e.m.) of duplicate samples. A repeat experiment yielded similar results.
Figure 19:
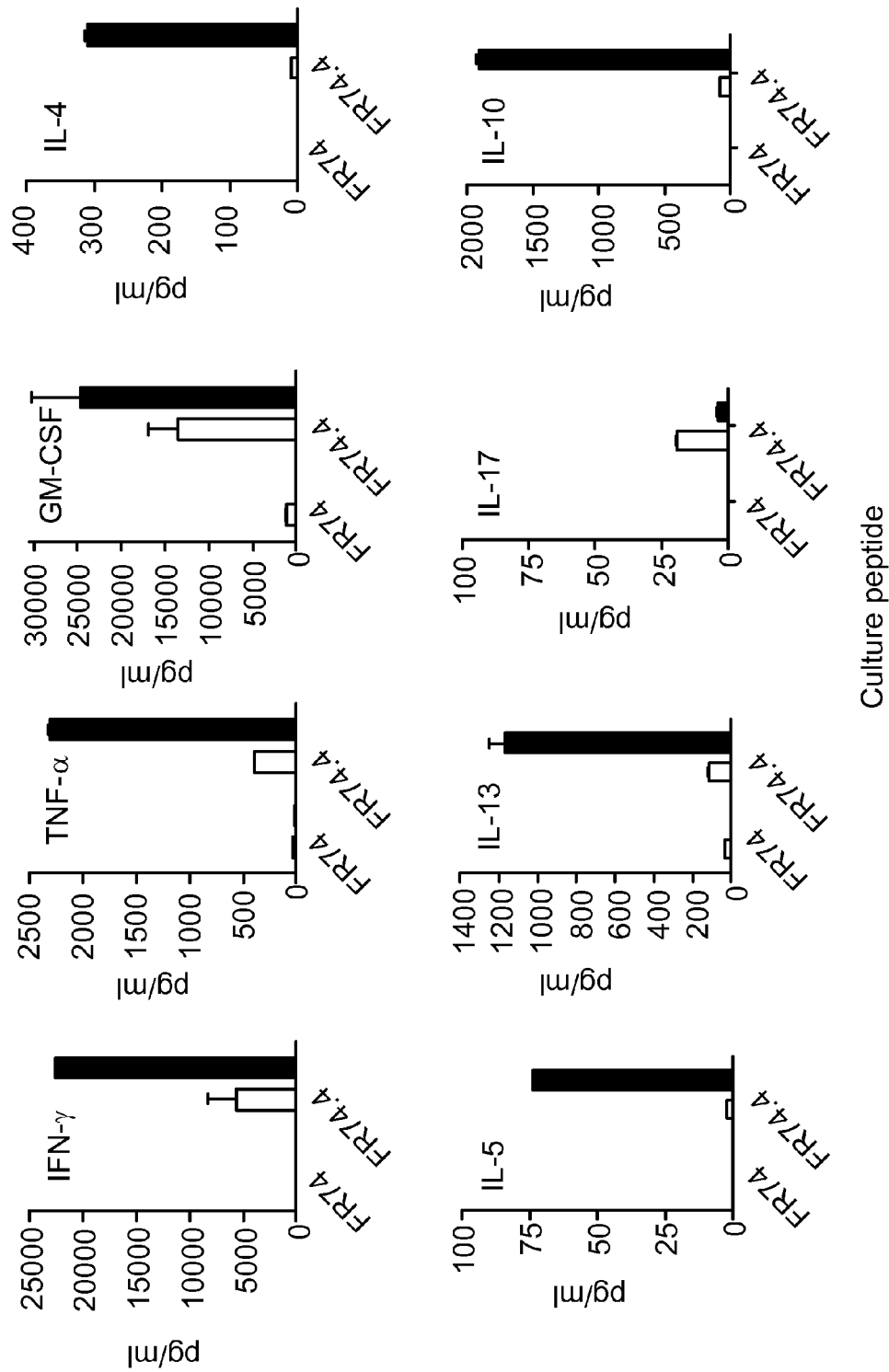
FIG. 19. Epitope nesting does not select for specific T cell subsets. Panel shows concentrations of Th-1 (IFN-γ, TNF-α, and GM-CSF), Th2 (IL-4, IL-5, and IL-13), Th17 (IL-17) and regulatory (IL-10) cytokines Shown are cytokine concentrations from supernatants of purified CD4 T cell line generated with either polypeptide-pulsed (either FR74 or FR4.4) DC. Cytokines were measured following stimulation of cells with splenocytes pulsed with either no antigen (open bars) or native FR74 polypeptide. To avoid contamination of cell culture supernatants with splenocyte-derived cytokines, the T cells were purified from the splenocytes prior to incubation to measure cytokines Each bar is the mean (±s.e.m.) of duplicate samples. Results are representative of 2 experiments.
Figure 20:
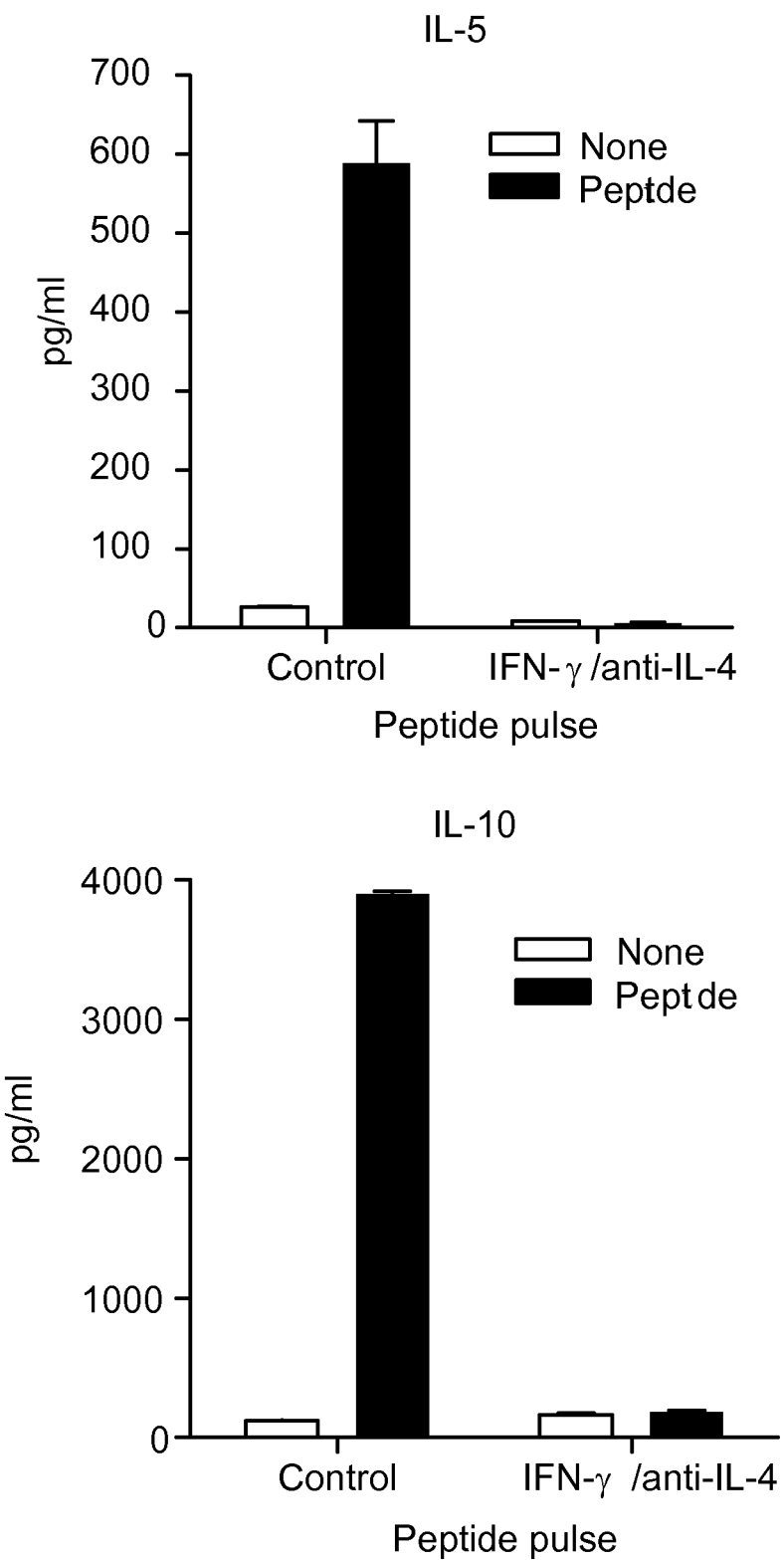
FIG. 20. Manipulation of culture conditions can reduce levels of IL-5 and IL-10 secreting Th cells. Shown are the concentrations of IL-5 and IL-10 within T-cell culture media following simulation of Th cells with or without peptide antigen. Each bar is the mean (±s.e.m.) of duplicate samples.

Another potential reason for the enhanced T cell activation is that epitope nesting results in enhancement of cytokines that facilitate the induction of T cell activation. To test this hypothesis, purified bone marrow-derived DC were incubated with native FR74 or with FR74.4 followed by analysis of the DC culture supernatant using cytokine multiplexing. Standard cytokine kits were obtained from BioRad, and used to measure the following cytokines in the pg/mL concentration range: IL-1α, IL-1β, IL-2, IL-3, IL-4, IL-5, IL-6, IL-10, IL-12p70, IL-17, IL-13, IL-23, IFN-γ, GM-CSF, MIP1-α, TNF-α and VEGF. No T cell-specific cytokines (underlined) were produced by the DC, demonstrating little to no T cell contamination. Of the remaining cytokines, the nested epitope enhanced the release of IL-1α, IL-6, and IL-12p70 as demonstrated in FIG. 14. Of the chemokines in that panel (i.e., CXCL10, CCL11, CXCL1, CCL1, CCL7, and CCL5), epitope nesting resulted in the elevated levels of CCL7, CXCL1, and CXCL10 (FIG. 15).

Overall, the results provided herein establish a versatile model system to begin understanding how epitope nesting can be used to rapidly generate Th cell lines that contain high avidity fully functional, young T cells potentially suitable for adoptive T cell therapy. In summary, ex vivo activation of antigen-specific Th cells can be greatly facilitated by N- and/or C-terminal modification of MHC class II polypeptides. Interestingly, each single modification exhibited a unique mechanism of action, which is additive or synergistic depending on the outcome measure.

Determining the Optimal Structural Requirements of Epitope Nesting for Maximal Ex Vivo Generation of Antigen-Specific Th Cells The following is performed to determine the linear configuration of the Ii-key linker that results in optimal MHC class II exchange. FIG. 16 describes the modifications for the model FRα polypeptide, FR74, where the length of the flexible linker region is varied. The polypeptide to be displaced is the previously established I-A$^q$-restricted polypeptide, p254-268 (Bayrak et al., $Int.$ $Immunol.$, 9(11):1687-99 (1997)), which is derived from mouse type II collagen. I-A$^q$ is purified from concanavalin A-activated FVB/N splenocytes. FVB/N mice do not express measurable levels of I-E$^q$, thus diminishing the possibility of contamination by other MHC class II molecules in this assay. $2\times10^{10}$ activated splenocytes are lysed in a solution of 0.1% Nonidet P-40 in PBS (pH 7.4). The MHC class II molecules are then isolated with an anti-MHC class II affinity column. The detergent is exchanged for 0.2 mM dodecyl maltoside to preserve class II stability as described elsewhere (McFarland et al., $Proc.$ $Natl.$ $Acad.$ $Sci.$ $USA$, 98(16):9231-6 (2001)). Free MHC polypeptides are then incubated with 5 µM FITC-labeled p254-268 at pH 5.3 in PBS with citrate-phosphate buffer at 37° C. overnight. Size exclusion chromatography is used to remove the free polypeptide, and the separated complexes are diluted in excess unlabeled free polypeptide with or without Ii-key modifications and incubated for varying times followed by size exclusion chromatography in Centri-spin (Princeton Separations, Adelphia N.J.). Peptide free buffer is used as control. The linked peptides are compared with solutions of exchange peptide and epitope that are unlinked. The reactions are carried out at 37° C. for varying times, and which time the fluorescence of the free peptide solution is measured in a Victor 1420 Multilabel counter (Perkin Elmer), and the relative rates of dissociation are calculated from a standard curve based on free FITC labeled p254-268 of known molarity. Each assay is done in triplicate so that statistical comparisons can be made to conclusively address the hypothesis.

To Determine the Optimal Furin Sensitive Linker Required for Enhanced Ex Vivo Activation of Antigen-Specific T Cells Mediated by DC3

To minimize reactivity to a potential frameshift epitope within FR74.3 due to the addition of the relatively long DC3 peptide, a furin sensitive linker is incorporated between DC3 and the FR74 epitope. Furin is a ubiquitously expressed proprotein convertase (endoprotease) that is known to be involved in the activation of a number of proproteins. It is a membrane spanning enzyme with a relatively short cytosolic motif that localizes the enzyme to the trans-Golgi network and endosomal system. In this experiment, the goal is to address the hypothesis that furin is required for enhanced ex vivo activation of Th cells and the optimal furin linker.

In order to determine whether furin cleavage is required, two methods are used: furin insensitive linkers and furin inhibitors. Blockade of enhanced ex vivo expansion mediated by the DC3 peptide using these two methods is powerful evidence, outside of a furin knockout mouse, that furin is required for the actions of DC3. Although it has already been shown that DC3 must be linked to antigen, as a control T cells are expanded using free FR74 mixed with free DC3. To test the role of furin with furin-insensitive linkers, RARR (SEQ ID NO:4) is replaced with VRVV (SEQ ID NO:41) with the polypeptides FR74.1, FR74.3, and FR74.8 as shown in FIG. 17. In parallel with these cultures, cultures are included in which inhibitors are included. The stoichiometric peptidyl inhibitor decanoyl-Arg-Val-Lys-Arg-CH2CL (SEQ ID NO:42) and α1-antitrypsin Portland, which are the two most commonly used inhibitors, are employed. While decanoyl-Arg-Val-Lys-Arg-CH2CL (SEQ ID NO:42) is not selective, α1-antitrypsin is highly selective for furin with a Ki=600 pM. Cultures are examined over a range of concentrations of inhibitors and assayed as described with ELIspot and proliferation assays. To generate Th cells, $CD4^+$ T cells are purified by incubation of splenocytes with anti-$CD4^+$ MACS microbeads (Miltenyi, Auburn, Calif.) for 20 minutes at 4° C., followed by positive selection of $CD4^+$ T cells using an AutoMACS automatic magnetic cell sorter according to the manufacturer's specifications. Th cell lines are established with bone marrow derived DC at a concentration of $5\times10^4$ T cells/mL in 24-well tissue culture-treated plates in complete medium on day 0. To derive the dendritic cells (DCs), bone marrow is harvested from the long bones of FVB/N mice and seeded in 6-well plates ($3\times10^6$/well) in complete media with murine GM-CSF (10 ng/mL) and IL-4 (1 ng/mL). Media and cytokines are replaced after 3 days. On day 5, CPG is added to the cultures at 1 μg/mL, and the cells are ready for T cell induction on day 6. The tissue culture-generated DC are pulsed with 10 μg/mL FR74 peptide or its modifications and 10 μg/mL B7DC-crosslinking antibody at 37° C. for 4 hours. In these experiments, constant mass is maintained. Next, the peptide-loaded DC are washed with media, and the CD4+ T cells are added, and on days 8 and 10, IL-2 (50 U/mL) is added. On day 15, cells are assayed. For the ELIspot analysis, anti-IFN-γ (Pharmingen) antibody is added to a 96-well nitrocellulose-backed plate (NC-plate, Millipore) at 50 μL/well at a concentration of 10 μg/mL in PBS and incubated overnight at 4° C. The day of analysis, the NC-plate is washed with PBS and blocked for 1-2 hours at 37° C. with PBS/2%BSA. After blocking, the plate are again washed. The Th cells are transferred to the antibody-coated plates. Syngeneic naïve CD4 T cells alone without peptide antigen are used as the negative control. Th cells are seeded at $5\times10^4$ cells/well with a range of native (i.e., FR74) peptide, irrelevant peptide, FRαMMC tumor lysate, irrelevant tumor lysate, media or concanavalin A. Irradiated syngeneic splenocytes are added at $1\times10^5$ cells/well as antigen-presenting cells. The plate is incubated at 37° C. for 24 hours. The plate are washed with PBS/0.05% Tween-20, and 100 μL/well biotinylated anti-IFN-γ(5 μg/mL, Pharmingen) antibody are added to each well. The plate are incubated overnight at 4° C. After washing with PBS, streptavidin-AP (BioRad) is added at 50 μL/well at a 1:1000 dilution in PBS. The plate is incubated for 2 hours at room temperature (RT) followed by washing. AP color development solution (Bio-Rad) is added, 100 μL/well, and incubated at RT for 20-30 minutes. The plate are thoroughly rinsed under running tap water after which the plastic plate backing is peeled off, and the plate is allowed to dry completely. The spots, representing cytokine-secreting T cells, are counted in an AID ELIspot reader (Strassberg, Germany). Antigen-specific precursor frequencies are expressed as: (mean number of spots in antigen wells-mean # spots in no antigen wells)/total number of cells. To determine the proliferation, the T cells are seeded with antigen and antigen-presenting cells exactly as described above and incubated for 24 hours at 37° C. $^3$H-thymidine is then added at 1 µCi/well and incubated for another 24 hours. After incubation, the cells are harvested on a Filtermate harvester, and the filter membrane is dried and bagged with scintillation fluid. Radioactivity is counted on a Top Count NXT scintillation counter. The antigen-specific proliferation is calculated by subtracting background proliferation. All experiments are repeated 3 times to determine the reproducibility of the conditions in generating lines. Using ELIspot, actual numbers of antigen-specific cytokine secreting Th cells elicited over a range of concentrations of native antigen are directly quantitated which can be correlated with dissociation rates obtained above using linear regression analysis with the Graphpad Prism graphics program. Similar correlation approaches are used to assess the proliferation responses.

Should it be found that furin cleavage is required for the efficacy of DC3, future experiments can be performed to determine if there is an optimal cleavage sequence. The consensus sequence that furin cleaves at is -Arg-X-Lys/Arg-Arg- (SEQ ID NO:43), and the cleavage site is positioned immediately after the carboxyl terminus Arg. Although any amino acid is generally acceptable at P2, studies have shown that a basic P2 amino acid enhances processing (Krysan et al., *J. Biol. Chem.,* 274(33):23229-34 (1999)). While the current approach incorporates an alanine residue at P2, whether T cell expansion is improved is tested by incorporation of either an arginine (FR74.9) or lysine (FR74.10) in place of alanine A six amino acid cleavage site (RARYKR; SEQ ID NO:12) is tested in comparison with one of the four amino acid linkers (See FR74.11 in FIG. 17). Modifications that result in at least a 15% increase in T cell frequencies or thymidine incorporation and whose values are statistically different at $p<0.05$ are considered superior. If it is found that furin cleavage is not required, that would indicate that the furin linker acted merely as a linker, in which case a logical next set of experiments is to determine if there is an optimal linker configuration and/or length.

Identifying the Minimal Motif of DC3 that Mediates DC Binding

Identifying the minimal sequence of a DC3 peptide is important for three primary reasons. First, identification of shorter regions may assist in the identity of the receptor, which may bind with higher affinity to shorter regions. Secondly, knowledge of the sequence can permit mutational studies to improve the binding further. Further, the clinical application of the technology, whether in vaccine or adoptive T cell therapy, would benefit due to lower synthesis costs and regulatory concerns. In order to determine the minimal peptide, a two-pronged approach is used. In the first set, peptides are synthesized with three amino acid deletions and examined for uptake into DC (FIG. 18). The peptides contain an in-line biotin so that uptake is quantitated using streptavidin-phycoerythrin (PE) with flow cytometry, which is done as described elsewhere (Surman et al., *J. Immunol.,* 164(2):562-5 (2000)). Samples are run on a FACS Scan II and analyzed using Cell Quest software (Becton Dickinson, San Diego, Calif.). Values are considered significantly lower, compared to FR74.3 if they are below the mean and 2 standard deviations of the intensity obtained. An alternative strategy is to use only the DC3 peptide without attaching it to the MHC class II peptide. The strategy is to use the complete modified antigen. Once the minimal sequence is identified, a truncated DC3 peptide alone is synthesized, and it is compared to full length DC3. If the same pattern is seen with the DC3 peptide alone (i.e., without MHC class II peptide), then that is powerful evidence that DC3 acts independently of MHC class II binding. Once it is determined which of the 3 amino acids deletes the activity, the next step is to add back the amino acids singly until activity is regained, thus defining the minimal sequence. Lastly, it is confirmed that the binding activity of the truncated peptides is linked to the Th cell generation using proliferation and ELIspot analysis as described herein. Lastly, at this point, the design of the peptide is tentative.

Confirming that Dual Modifications Work Cooperatively to Enhance the Ex Vivo Generation of High Affinity Tumor Antigen-Specific Th Cells First, experiments are performed to determine whether the dually modified peptide is able to dissociate MHC class II bound to peptide with similar kinetics compared to the peptide with the single Ii-key modification. Experiments also are performed to determine whether the dually modified peptide is able to generate high avidity antigen-specific Th cells specifically evaluating for the generation of Th cells that proliferate in response to antigen levels as low as $10^{10}$-$10^{9}$ g/mL. In addition, the frequencies of the cells in the cultures are assessed using ELIspot.

It is expected that the dual modified peptide will generate approximately double the numbers of cells as assessed by ELIspot and, importantly, that the modifications will synergize to improve the avidity. Outcomes that are different than anticipated would likely reflect molecular interactions between the DC3 and Ii-key motif that were not anticipated, such as folding or coiling. If the enhanced activity is lost by combining the modifications, polypeptides with different modifications will be synthesized and tested.

A simple linker system was selected with stepwise addition of carbons to the linker backbone. Despite the fact that high affinity T cells are recruited in with the current linker, it is possible that other linker systems are more potent by either increasing the association rates or decreasing the dissociation rates, or both. One example of another flexible linker that can be used is as follows a $[GGSGGS]_n$(G=glycine and S=serine) linker system.

Another item is that Th subset skewing may occur which could cloud interpretations of the polypeptide modifications. Culture conditions used with the modified epitopes were found to not favor the expansion of one T cell subset over another (e.g., Th1 T cells, Th2 T cells) (FIG. 19). If evidence of skewing for one subset or another is found, then culture conditions that favor selection of one phenotype can be used. For example, FIG. 20 shows that the inclusion of IFN-γ and anti-IL-4 during T cell culture greatly reduces peptide-specific IL-5 and IL-10 secretion suggesting blockade of Th2 effectors and possibly $Foxp3^{+}$ Tregs.

The Molecular Mechanisms of Ex Vivo Activation of Antigen-Specific T Cells from Naïve Pools, Utilizing Nested Epitopes The hypothesis addressed in this section is that ex vivo generation of antigen-specific T cells from naïve pools using nested epitopes is dependent on Ii-key mediated peptide exchange and is a receptor mediated process involving increased peptide storage and enhanced chemokine/cytokine mediated communication between DCs and naïve T cells.

Determining if Epitope Nesting Enables the Generation of Antigen-Specific T Cells from Naïve Pools The inability to expand T cells from naïve pools can be an obstacle to the successful translation of adoptive T cell therapy. The capability of the nested epitopes to elicit antigen-specific T cells from naïve pools was tested. The results provided herein demonstrate that nesting results in the generation of antigen-specific T cells from naïve pools of T cells while no specific reactivity could be elicited with the native epitopes. The generation of antigen-specific T cells (especially anti-tumor T cells) from naïve pools can be particularly advantageous because such T cells would likely be further from senescence and would not have been previously tolerized by peripheral tolerance. Furthermore, using naïve T cell can permit ex vivo generation of central memory T cells, which can be long lived and can give rise to effector T cells.

The following is performed to test the hypothesis that nesting results in a better capability of generating antigen-specific Th cells from naïve pools. The first question that is addressed is whether the ability to expand for naïve pools requires both modifications, and the final peptide selection is guided as described herein. As described herein, DC are prepared and pulsed with peptides with single or dual modifications or without modifications. Purified (>97%) naïve CD4 T cells are stimulated with the DC. Following ex vivo expansion, it can be determined which of the peptides leads to induction of antigen-specific T cells using ELIspot and proliferation analysis as described herein. Th1 generation is used as a model for these studies and integrates additional studies to include cytokines and anti-cytokine antibodies. Finally, it can be determined if prior enrichment of the naïve fraction is necessary for optimal Th cell generation. To do this, naïve T cells can be isolated, and Th cell generation can be compared with non-naïve effector CD4 T cells (i.e., flow-through) or unselected CD4 T cells.

Determining if Ii-Key-Mediated Peptide Exchange Correlates with the Numbers and Avidity of Antigen-Specific T Cells Generated Ex Vivo Ii-key modification resulted in the generation of high avidity Th that can respond at levels of antigen near $10^{-8}$-$10^{-9}$ g/mL. A separate set of experiments are performed to test whether or not linker distance affects the generation of high affinity antigen-specific Th cells from naïve pools. Notably, experiments are performed to determine whether there is a direct correlation between the dissociation rates using linear regression analysis. Since we observed that cytokine (e.g. IFN-γ) release appears to be dissociated from proliferation, both proliferation and T cell frequency are assayed with ELIspot.

Figure 21:
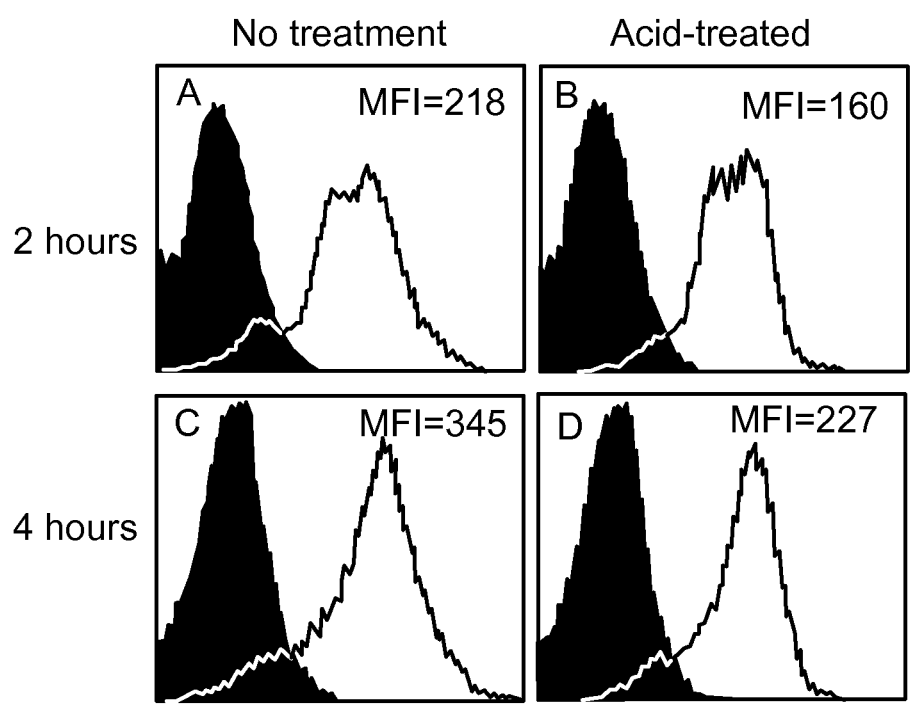
FIG. 21. Oregon green labeling is useful for assessing polypeptide storage in dendritic cells. Panels A-B and C-D show peptide-specific fluorescence (green trace) in DC pulsed with labeled FR74 polypeptide for 2 and 4 hours, respectively. Panel B and D show fluorescence in DC following acid washing to remove surface around polypeptide. Filled traces represent non pulsed DC. MFI=mean fluorescent intensity. Note that uptake was time dependent and that intracellular stores can be detected following acid washing.

Determining Whether DC3 Peptide Modification Enhances the Storage of Peptide Epitope Within the Dendritic Cell Endosomal Compartment Experiments are designed to test the hypothesis that the DC3 peptide results in enhanced storage of peptide apparently within DC depots that permit continued antigen presentation. To determine if the DC3 peptide enhances storage, the FR74 peptides (modified and native) are labeled with a fluorescent compound (Oregon green 488, Invitrogen Inc.) on the singular cysteine amino acid using a maliemide linker. As a control, FR74 is modified with a scrambled DC3 sequence. Maliemide-conjugated Oregon green 488 is reacted with peptides for 2 hours at room temperature followed by stopping with excess mercaptoethanol. Peptide is then purified by passage over G-10 PD Miditrap columns. Fluorescence of the equal volumes of each is assessed using a fluorescence spectrophotometer and mass spec analysis, to ensure consistent specific labeling of the cysteine residues. Because it is anticipated that the peptide will be localized to acidic endosomal or endolysosomal compartments, Oregon green will be used because under acidic conditions (pH 4-6) this dye maintains a high level of fluorescent emissions. The results of FIG. 21 demonstrate that the peptides can be labeled with this strategy and tracked within dendritic cells. DC is pulsed with labeled peptide (both native and DC3 modified) for varying times between 0 and 6 hours followed by a chase over the course of 16 hours to evaluate the kinetics of uptake and the diminution of signal. DC will be prepared from bone marrow as described herein. Rates of accumulation and loss of peptide will be calculated.

Figure 22:
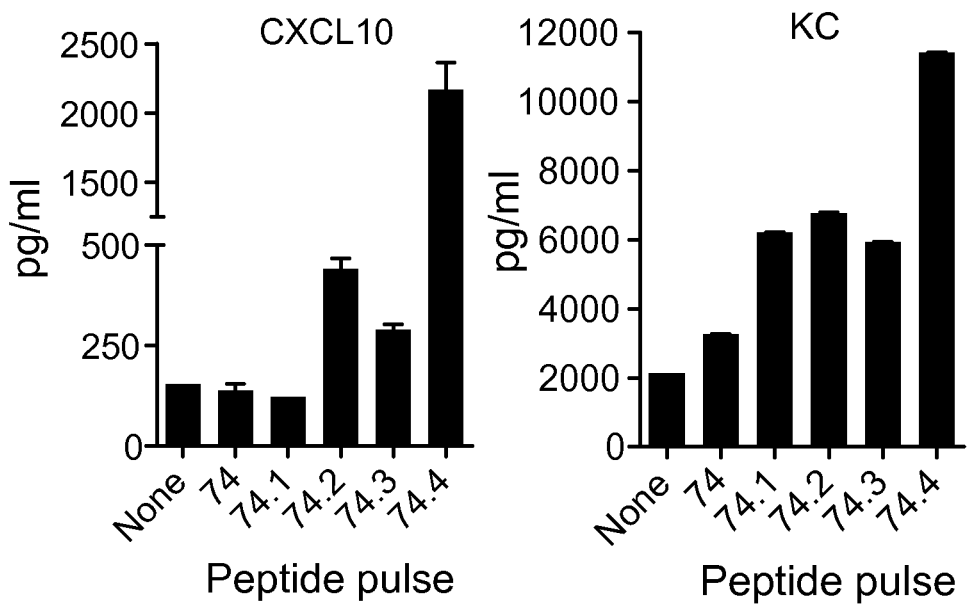
FIG. 22. DC pulsed with nested epitopes demonstrate higher chemokine secretion. Shown are the concentrations of chemokines within DC culture media 48 hours after pulsing with the indicated polypeptides. Each bar is the mean (±s.e.m.) of duplicate samples. A repeat experiment yielded similar results.

Determining Whether Optimal Ex Vivo Th Cell Expansion Requires Production of Chemokines or Cytokines by the Dendritic Cell The results provided herein show that DC pulsed with the dually modified peptide, FR74.4, produce significantly higher levels of the T cell attracting chemokines, CCL7 (MCP-3), CCL1 (KC) CXCL10 (IP-10) which could contribute to better ex vivo expansion. This hypothesis is tested using antibody neutralization. Neutralizing antibodies to each of these chemokines are available from R&D Systems (Minneapolis, Minn.), and the neutralization concentrations are established as per manufacturer's data sheet. In the first set of experiments, the goal is to determine which of the modifications (Ii-Key or DC3) results in the enhanced chemokine release. To do this, DC are prepared as described herein followed by pulsing with native peptide, singly modified peptides, or dual modified peptides for 2-4 hours. The peptides are removed following the pulse, and the DC are washed and resuspended in fresh culture medium. Twenty-four hours later, a sample of the supernatant is tested for accumulation of CCL1, CCL7 and CXCL10 using multiplex analysis examining the chemokines with kits and reagents available from BioRad (San Diego, Calif.). Briefly, Bio-Plex assay buffer is added to each well of a MultiScreen MABVN 1.2 μm microfiltration plate followed by the addition of the multiplex bead preparation. Following washing of the beads with the addition of 100 μL of wash buffer, 50 μL of the samples (i.e., cell culture supernatants) or the standards is added to each well and incubated with shaking for 30 minutes at room temperature. Standard curves are generated with a mixture of cytokine standards over a range of 0-32,000 βg/mL. The plate is then washed followed by incubation with pre-mixed detection antibodies. The plate is further washed, and 50 μL of streptavidin solution is added to each well and incubated with shaking for 10 minutes at room temperature. The beads are given a final washing and resuspended in 125 μL of Bio-Plex assay buffer. Cytokine levels in the sera are quantitated by analyzing 100 μL of each well on a Bio-Plex using Bio-Plex Manager software (ver.4.). It is anticipated that these results will reveal which moiety of the engineered FR74.4 peptide, either Ii-key or DC3, is mediating enhanced release of the chemokines. The results provided in FIG. 22 indicate that each of the peptides may have some intrinsic activity, which when combined results in synergistic production. The data obtained in these experiments, in and above identifying which of the modifications is responsible for enhanced chemokine production, can also determine the concentrations of each chemokines, a value which can be used to identify the neutralizing antibody concentration. Both the DC and the T cells can be assessed for expression of the receptors using flow cytometry.

Figure 23:
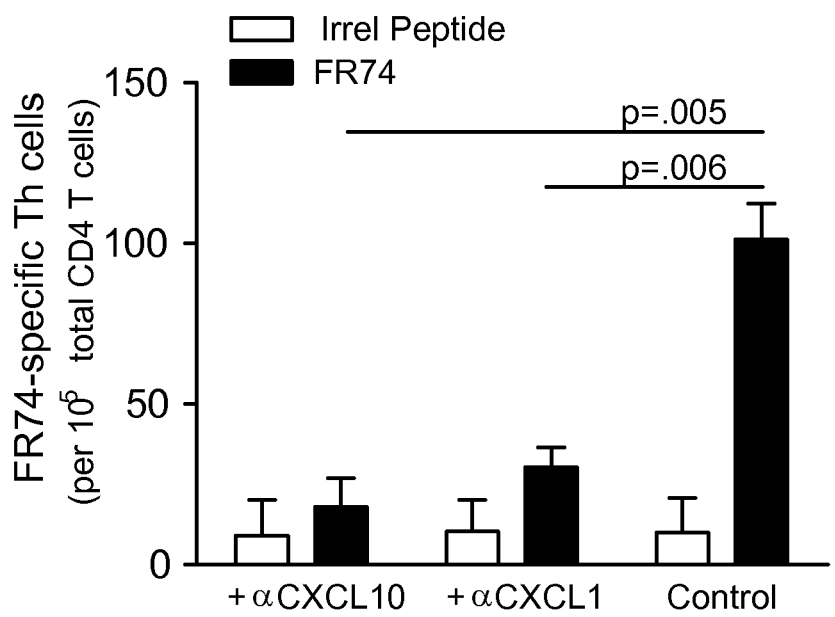
FIG. 23. T cell expansion requires DC produced CXCL10 and CXCL1. IFN-γ ELIspot analysis of FR74-specific T cells generated with FR74.4-pulsed DC in the presence of anti-CXCL10 antibody, and anti-CXCL1 antibody, or non-specific murine IgG (control). Results are the mean (±s.e.m.) of 3 replicates.

For the antibody neutralization experiments, DC are generated as described herein and pulsed with the modified peptides for 2-4 hours. The peptides are then washed away, and the media is replaced containing either control antibody or anti-chemokine antibodies. The amount of antibody added is based on the concentrations of chemokines released into the media as determined above and by the $IC_{50}$. Following culture, the T cells are examined by ELIspot and proliferation analysis to determine the role of each of the three chemokines Initial experiments with antibody blockade suggested involvement of CXCL1 and CXCL10 in the efficacy of the nested epitopes (FIG. 23). In that experiment, purified CD4 T cells were activated with FR74.4-pulsed DC in the absence or presence of anti-CXCL1 or anti-CXCL10 antibody. Control T cells received nonspecific murine IgG. After 12 days in culture, IFN-γ ELIspot was used to assess whether chemokine blockade impacted expansion. The results revealed nearly complete blockade of T cell generation by incorporation of either of the antibodies. Corroborating evidence can be obtained by blocking the receptors that bind to the chemokines being examined.

In reiteration of the above data, it was observed that modified FR74.4 selectively induces expression of IL-1α, IL-6, IL-12p70, IL-13 and TNF-α. A study revealed that the enhanced cytokine release results from synergism between the two modifications. Two examples are IL-6 and IL-12p70 as shown in FIG. 24. Note that while the IL-6 response is largely attributable to the Ii-key modification, the DC3 peptide, while ineffective itself, further stimulated levels of the cytokine In contrast, IL-12p70 was only elevated when both modifications were present on FR74. Initially, it is determined which of the modifications lead to the induction of these cytokines, followed by determining whether the cytokines have a role in driving enhanced T cell responses ex vivo. Antibodies to all of the elicited cytokines are commercially available and methods to identify the role of the cytokines can be identical to those described above evaluating the chemokines Determining the Therapeutic Efficacy of High Avidity Th Cells Generated with Nested Epitopes The following are performed to confirm that Th cells generated ex vivo with nested epitopes are therapeutic in murine models of cancer.

Figure 25:
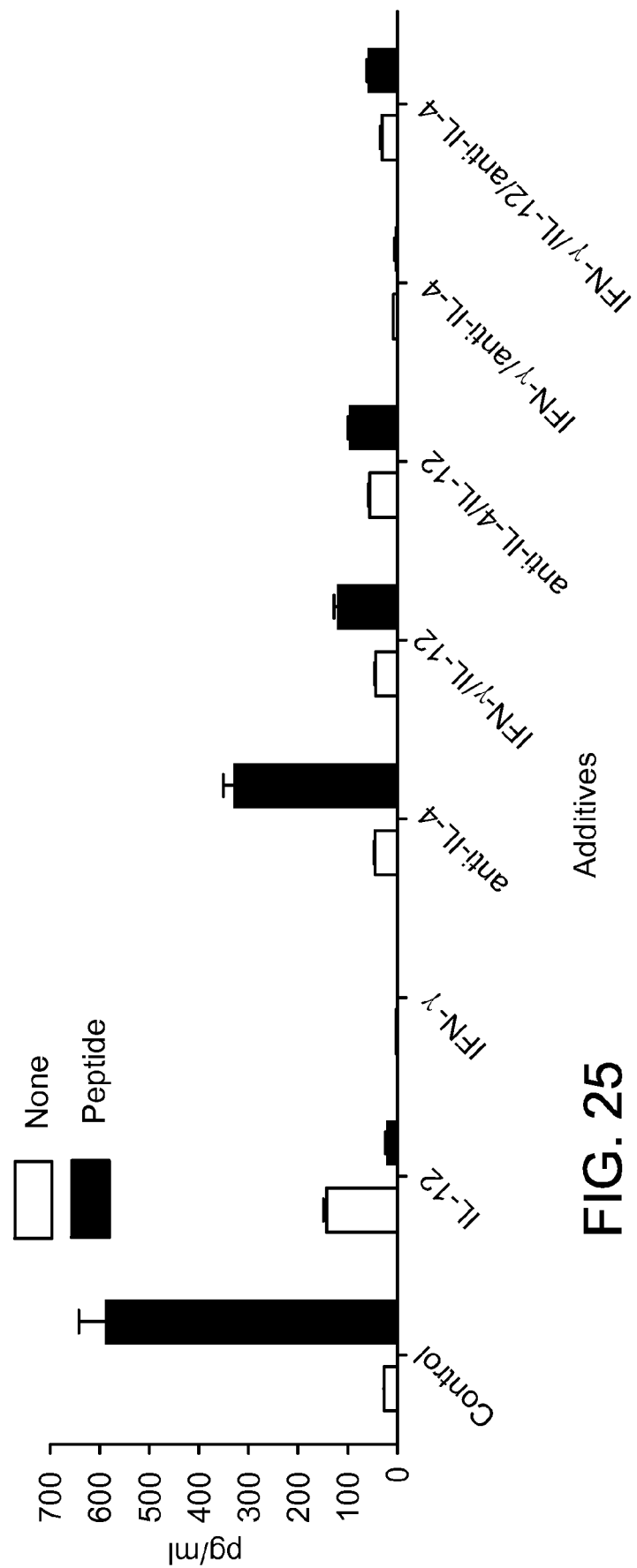
FIG. 25. Manipulation of culture conditions can reduce levels of IL-5 secreting T cells. Shown are the concentrations of IL-5 within T cell culture media following stimulation of Th cells with or without polypeptide antigen. Each bar is the mean (±s.e.m.) of duplicate samples.
Figure 26:
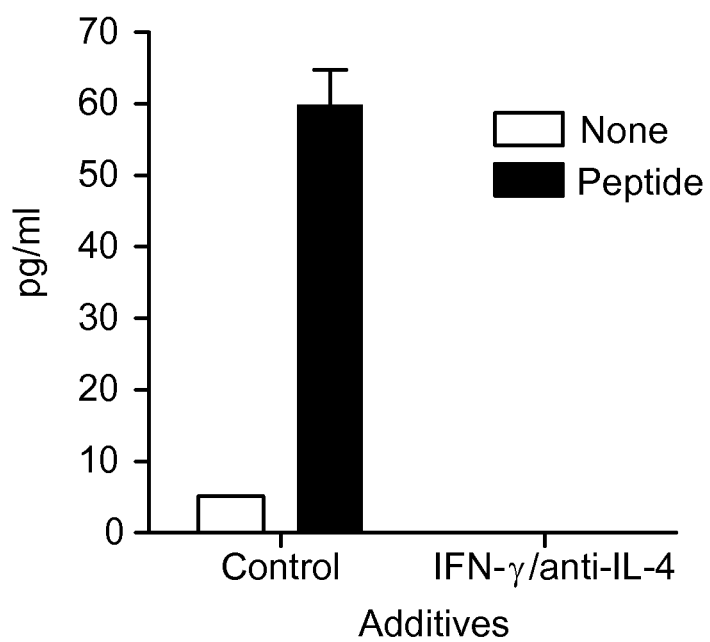
FIG. 26. Inclusion of IFN-γ, blocks generation of IL-17-secreting Th cells. Shown are the concentrations of IL-17 within T cell culture media following simulations of Th cells with or without polypeptide antigen. Each bar is the mean (±s.e.m.) of duplicate samples.
Figure 27:
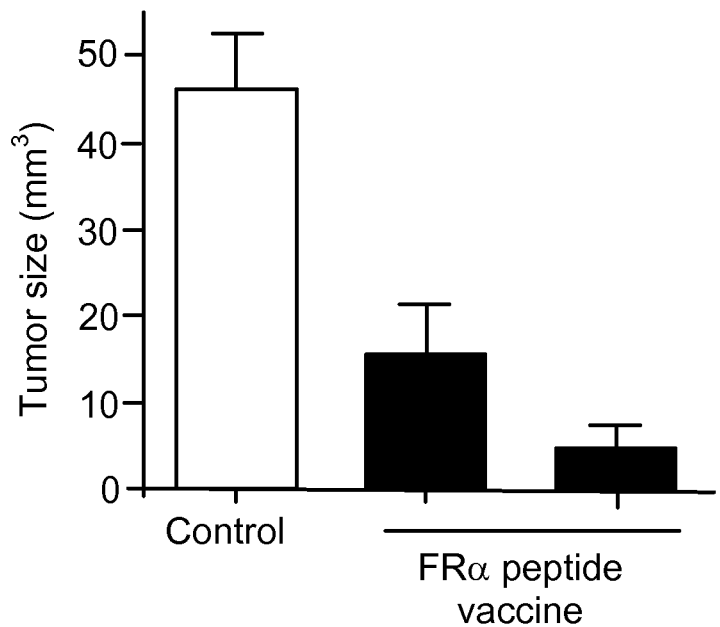
FIG. 27. Immunization with a FRα polypeptide mix reduces tumor growth in the Neu-tg mouse. Neu-tg animals were immunized two times with a PBS alone (control), or pool (25 or 13 μg/polypeptide, 4 polypeptides total) of predicted MHC class II epitopes. 7 days following the final vaccination, animals (3/group) were injected with a $2\times10^6$ live breast MMC tumor cells and 36 days following tumor injection tumor size was measured.
Figure 28:
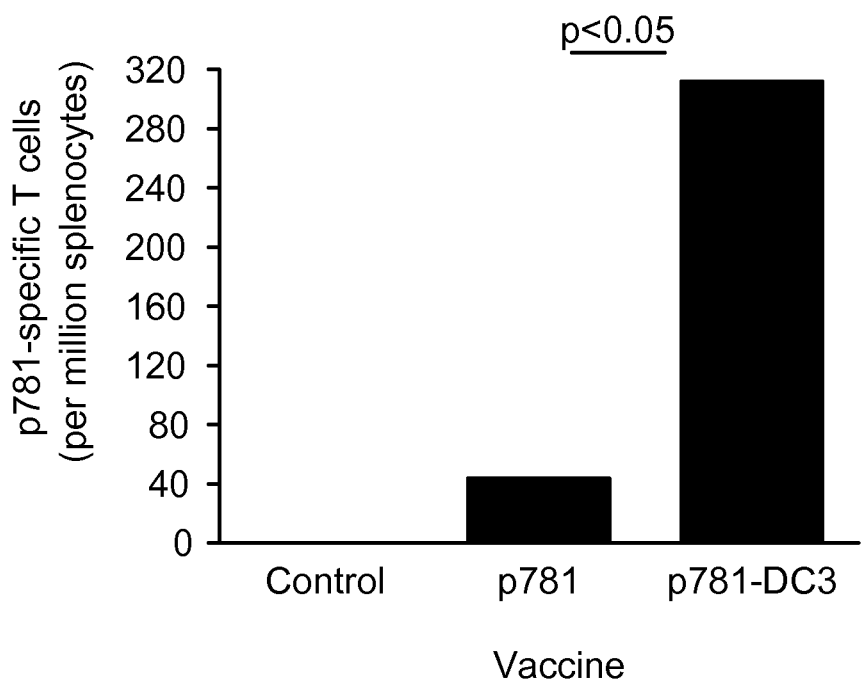
FIG. 28. Polypeptide modifications enhance expansion of tumor antigen-specific T cells. Panel shows IFN-γ ELIspot responses to rat-neu derived polypeptide, p781 in the splenocyes from 3 mice immunized with DC3 peptide (control), native peptide p781, or p781-DC3 along with GM-CSF as adjuvant.
Figure 29A:
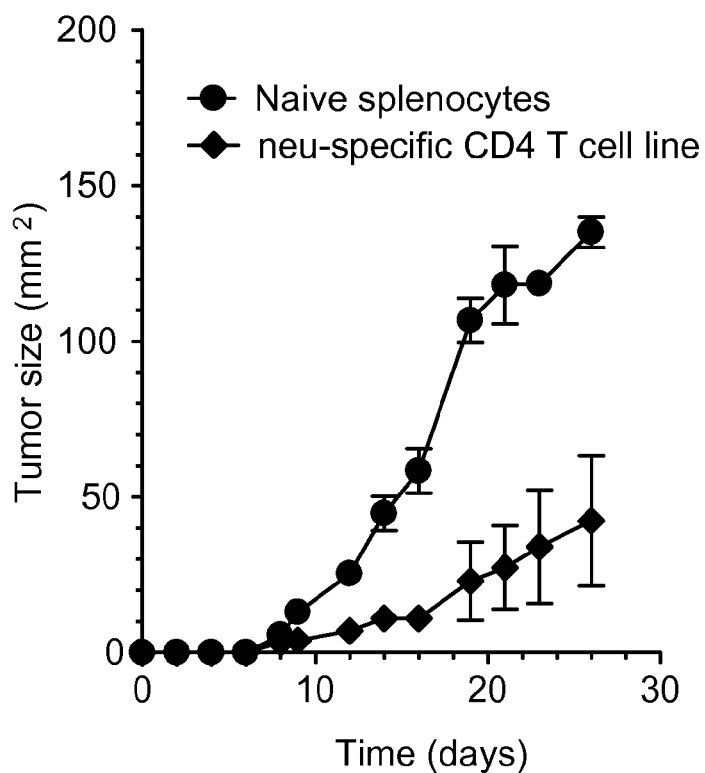
FIG. 29. Adoptive T cell therapy with tumor-specific CD4 Th cells suppresses tumor growth. Panel A. T cell lines were generated ex vivo and infused ($5\times10^6$) 24 hours after tumor challenge ($6\times10^6$ on day 0). Neu-tg mice were injected with normal splenocytes (circles) or with neu peptide p1166 cells derived from neu-tg mice (diamonds). Each data point is the mean measurement from 3 mice (±s.e.m.). Panel B. Shown are the IFN-γ ELIspot responses of a neu peptide p1166-specific CD4T cell lines. The data are presented as the mean (±s.e.m.) number of spots observed per wall. MMC are neu-overexpressing tumor cells, and ANV are neu-negative tumor cells. Both tumor cell lines are derived from mammary tumors in neu-tg mice.
Figure 29B:
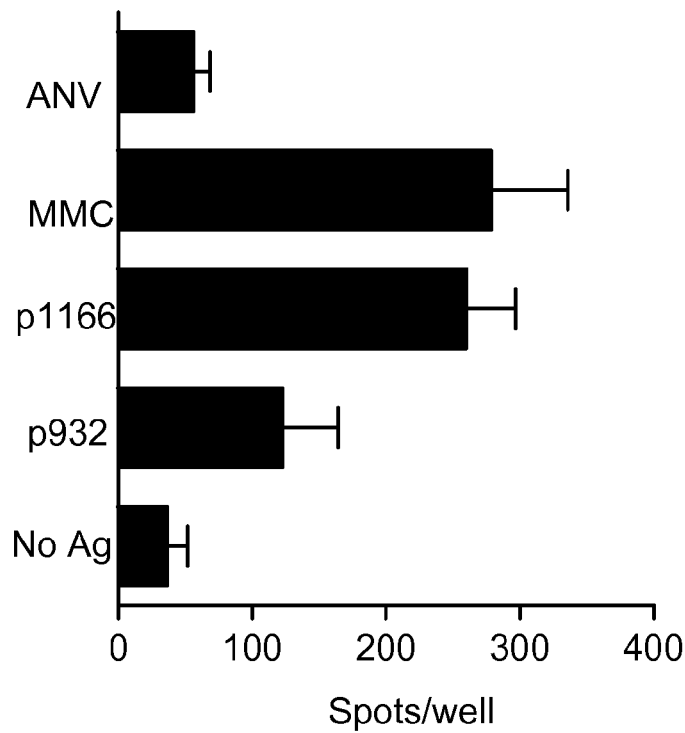

Determining Whether Th1, Th2, or Th17 T Cells can be Preferentially Expanded with Nested Epitopes by Altering the Cytokine Microenvironment Results shown in FIG. 25 demonstrate the capability of blocking Th2 immune effectors. In that experiment, cells were incubated with FR74.4 with DC and IL-2 (considered control) and also under various conditions which included combinations of IFN-γ, anti-IL-4, and IL-12. As shown, control cultures contained substantial levels of Th2 effectors which appeared to be completely blocked by the inclusion of either IFN-γ alone or in combination with anti-IL-4. Th1 immunity was retained. Both ELIspot analysis and proliferation assays are used to determine if blockade of specific subsets results in both augmented numbers and proliferative response. CD4 T cell cultures are established as described herein, and depending on the comparisons, cultures can be established from either naïve or unselected CD4 T cells. To selectively generate Th1 immune effectors, IFN-γ is used at 2 ng/mL along with anti-IL-4 (10 μg/mL) which blocks Th2 and Th17 cells (FIGS. 25 and 26). For Th2 induction, 1 ng/ml IL-4, anti-IFN-γ, and 10 μg/mL anti-IL-23 are used. Lastly, since there is a plan to determine the therapeutic efficacy of Th17 cells, 5 ng/ml IL-23, 10 μg/mL anti-IL-4, and 25 mg/mL anti-IFN-γ is used. If a specific condition does not block the effectors which it is intended to block, the conditions are modified by increasing the amounts of antibodies or cytokines Determining the Numbers of Th Cells Required for an Anti-Tumor Response in Murine Models of Cancer The hypothesis is that adoptive T cell therapy can be used to eradicate residual "disseminated-like" disease as well as established "bulky" disease. These studies will also have implications for the treatment of other diseases as well, such as post-transplant viral reactivation diseases. In this section, one goal is to determine the numbers of Th cells, generated with nested epitopes, required for tumor eradication. Fortunately, given the species and MHC background indifference of our approach, many models are available to address this. One model that is routinely used in the laboratory is the FVB/N based neu-transgenic mouse. These mice develop tumors due to overexpression of the rat neu protein in the mammary gland and as stated in the results, the tumors also express FRα. Thus, this work is translated directly into this model. The evidence suggests that FRα is an antigenic target in this mouse model as shown in FIG. 27. In that experiment, animals were immunized with one of two doses of a peptide vaccine consisting of a pool of FRα derived peptides followed by tumor challenge. As shown, tumor protection was observed. An alternative approach would be to modify rat neu peptides. Two neu helper peptides were identified, p781-795 and p1166-1180, that can be used as the target antigen and as with the FR74 model peptide, modifications improve immunogenicity as shown in FIG. 28. In that experiment, neu-peptide p781 was modified with DC3 and tested for the ability to generate T cells in vivo. In addition, it was observed that Th cell lines can be infused to prevent tumor growth in this mouse model, an example of which is shown in FIG. 29, neu-specific Th cells with therapeutic activity can be generated ex vivo.

A couple of different models were developed in the neu-tg mouse. The first model is the minimal disease model which would be analogous to the patient that would have had most of their tumor "debulked" by standard therapies but still have tumor deposits remaining. In this model, T cells are infused shortly after a tumor challenge, prior to establishment of a palpable tumor. A cell line MMC, which can be used to establish tumor, was developed. The expected outcome of the experiments in the minimal disease model would be prevention or arrest of continued growth of tumors. The other model is the established disease model. This model would be analogous to the patient who would have a large measurable tumor burden that cannot be removed surgically or by other means such as radiation therapy or chemotherapy. In this model, the Th cells would be infused after the tumor has reached a size of approximately 4 mm$^2$. Thus, regression could be adequately monitored. Experiments described herein aim to determine the numbers of Th cells required to inhibit or eradicate neu-overexpressing tumors.

In the minimal disease model, after the administration of $1\times10^6$ cells subcutaneously, 100% of animals injected will develop rat neu-mediated tumors between 18-20 days after tumor implant. Groups of non-immunized syngeneic neu-tg mice are given tumor at a dose of $1\times10^6$, followed in 24 hours by intravenous transfer of ex vivo expanded Th1, Th2, or Th17 cell lines in a dose escalation with $1\times10^5$, $1\times10^6$, or $1\times10^7$ T cells. The Th cell lines are generated as described herein, but priority is given to those strategies that yield the best ex vivo response. In the established disease model, after the administration of $6\times10^6$ cells subcutaneously 100% of animals injected will develop rat neu mediated tumors between 8-10 days after tumor implant. When the tumors reach approximately 4 mm$^2$, Th1 cells are infused by tail-vein injection. Naïve CD4 T cell infusion is used as negative controls. In both models, mice are evaluated for tumor growth by size every 2-3 days. Whether there is a correlation between number of Th cells infused and the amount of tumor reduction or inhibition can be tested. The number of Th cells to be infused is categorized into 4 distinct groups, none, $10^5$, $10^6$, or $10^7$. Tumor reduction is examined both as a binary outcome (success vs. failure, with success defined as no evidence of disease) and a continuous outcome (reduction as a percentage). The Kruskal-Wallis test is used to compare the amount of tumor reduction between the 4 groups, and the chi-square test is used to compare the proportion of successes between the 4 groups. In a pilot study, 5 animals in each group are treated, and the resulting estimates are used to estimate the sample size required to test the null hypothesis that no association exists. The alternative hypothesis is determined by a combination of what is clinically important and what the pilot data suggest.

Antigen-specific Th cells are monitored in the spleen and tumor using ELIspot analysis specific for Th1, Th2, or Th17 (depending on the phenotype of the line infused) in order to determine the frequency and persistence of the cells. Neu-specific CD8+ responses can be evaluated using IFNγ ELIspot analysis of isolated CD8+ T cells from experimental animals treated with adoptive Th cell therapy (all subsets, Th1, Th2, and Th17). Spleen and tumor-draining lymph nodes are harvested from neu-tg mice treated with control CD4 T cells or Th cell lines. CD8+ cells are purified by incubation of T cells with anti-CD8+ MACS microbeads (Miltenyi, Auburn, Calif.) for 20 minutes at 4° C., followed by positive selection of CD8+ T cells using a VS column with a MACS magnet according to the manufacturer's specifications. The purity of the T cells is determined by staining cells with fluorochrome-labeled CD4-, CD8-, and CD3-specific antibodies (Becton Dickinson, San Jose, Calif.) followed by flow cytometry analysis. CD8+ T cells are examined by ELIspot analysis as described above using tumor cells as stimulators. A neu-negative sygeneic cell line is used as a negative control for MMC. It is anticipated that we should be able to measure CTL responses that are generated as a result of infusion of antigen-specific Th cells as compared to controls. It can be determined whether there is a neu-specific antibody response which may be the most visible following infusion of Th2 cells. This is measured by standard capture ELISA techniques. Collectively, these investigations will determine if Th cell therapy is an active therapy (i.e., generates endogenous immune responses).

Determining Whether Th Cells Generated with Nested Epitopes are Able to Cooperate with Other Common Immunotherapies Experiments can be performed to determine whether infusion of antigen-specific Th is able to enhance the efficacy of infusion of CTL lines specific for rat neu $H2^q$ peptide, p420-429. CTL lines specific for this peptide are done by immunizing mice with peptide and CpG as described elsewhere (Nava-Parada et al., *Cancer Res.*, 67:1326-1334 (2007)). CD8 T cells are harvested and grown essentially as described elsewhere (Knutson and Disis, Hum. Immunol., 63(7):547-57 (2002)). Groups of 5 tumor-bearing mice are infused with peptide-specific T cells or freshly isolated naïve CD8 T cells with or without the best dose of Th cells. Tumors are monitored as described herein. Results from these mice are used to calculate an approximate sample size that would determine whether the effects of both cell lines are additive or synergistic. A synergistic result suggests a helper effect mediated by which could then be verified by evaluating whether or not infusion of Th cells promoted the expansion and or persistence of CTL by tetramer analysis. In addition to CTL therapy, whether or not Th cell infusion can collaborate with neu-specific antibody therapy can be examined. To examine whether Th cell infusion can collaborate with antibody therapy, mice are challenged with tumor, which is allowed to grow for about 8-10 days after which time antibody therapy (30 μg/injection) will begin along with an infusion of Th cells. Antibody therapy continues every 3 days for 30 days, and tumors are regularly measured. Again, groups of 5 mice are treated with antibody, antibody+Th cells, Th cells alone, or left untreated. Following treatment, one examines for an effect with which to calculate an accurate sample size to detect a difference. Statistical analysis is done as described herein.

Example 2

Use of Nested Epitopes as Cancer Vaccines

Figure 32A:
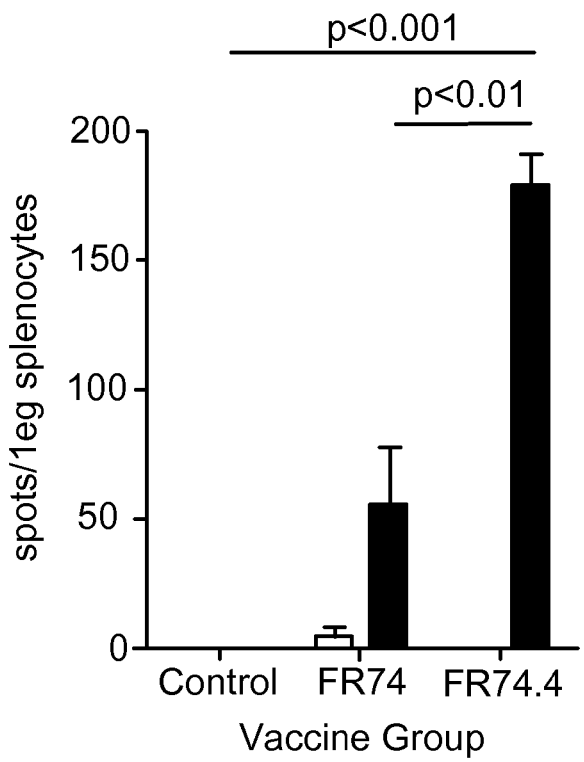
FIG. 32 contains two graphs plotting results that demonstrate that nested epitopes are more immunogenic than native epitopes when used as vaccines in tumor bearing mice as measured using an ELIspot assay. Each bar is the mean of three mice, each done in triplicate. P values, comparing FR74-specific responses, were calculated using Tukey-Kramer Multiple Comparisons test.
Figure 32B:
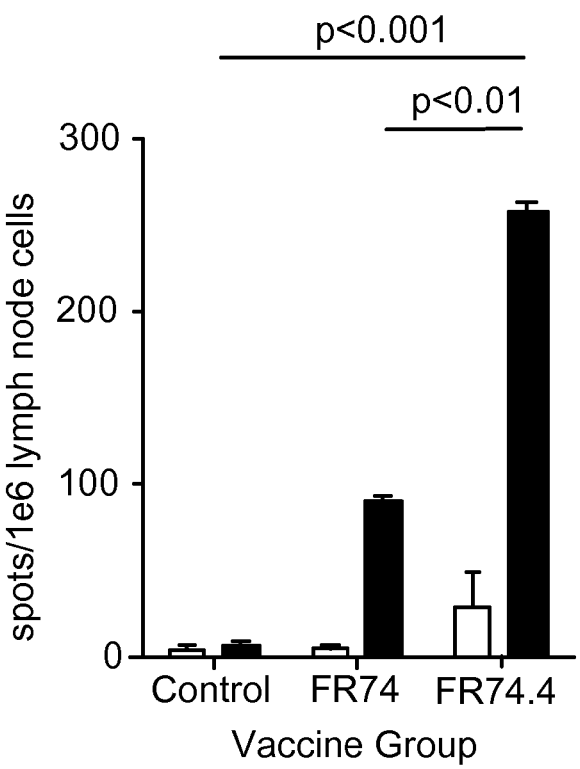
Figure 33A:
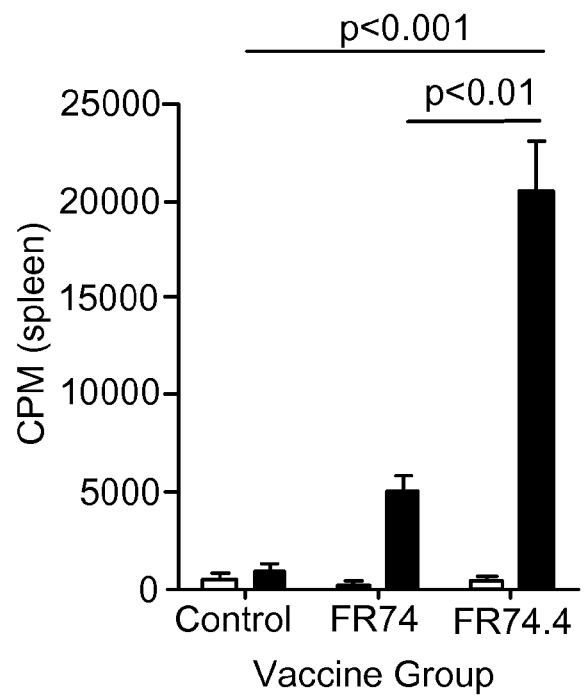
FIG. 33 contains two graphs plotting results that demonstrate that nested epitopes are more immunogenic than native epitopes when used as vaccines in tumor bearing mice as measured by proliferation. Each bar is the mean of three mice, each done in triplicate. P values, comparing FR74-specific responses, were calculated using Tukey-Kramer Multiple Comparisons test.
Figure 33B:
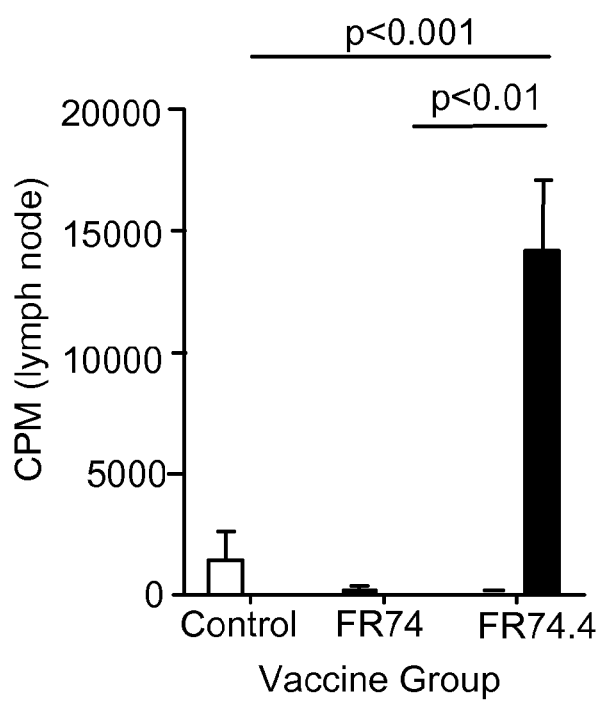

Mice were implanted with ovarian tumor and 10 days later were treated with PBS, native epitope FR74 (2150 μg/kg in 100 μL injected at the base of the tail), or nested epitope FR74.4 (5000 μg/kg in 100 μL injected at the base of the tail) over the course of a week. On day 50, the mice were sacrificed and spleen, lymph node, and tumor tissue was harvested. T cell responses and tumor weights were then estimated. The number of FR74-specific T cells in the spleens and lymph nodes was determined (FIG. 32). T cells were estimated using an IFN-γ ELIspot assay testing responses against native FR74 (black bars) or an irrelevant peptide (white bars). In addition, the proliferation of T cells, in response to native FR74 (black bars) or an irrelevant peptide (white bars), was measured in the spleens and lymph nodes (FIG. 33). T cell proliferation was estimated using a tritiated thymidine assay. These results demonstrate that the nested epitope was more immunogenic than native epitopes when used as vaccines in tumor bearing mice.

Figure 34C:
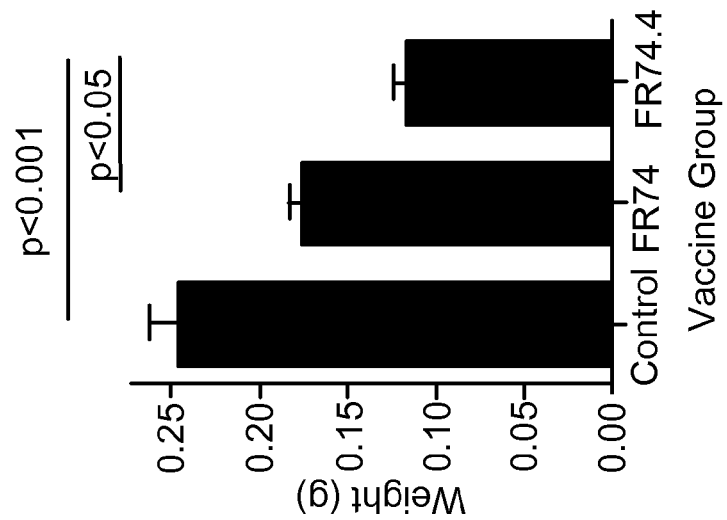
FIG. 34 contains three graphs plotting results that demonstrate that immunization of ovarian cancer-bearing mice with nested epitopes results in tumor eradication and infiltration of FR74-specific T cells that retain proliferation. Each bar is the mean of 3 mice, each done in triplicate. P values, comparing FR74-specific responses or tumor weights, were calculated using Tukey-Kramer Multiple Comparisons test.
Figure 34B:
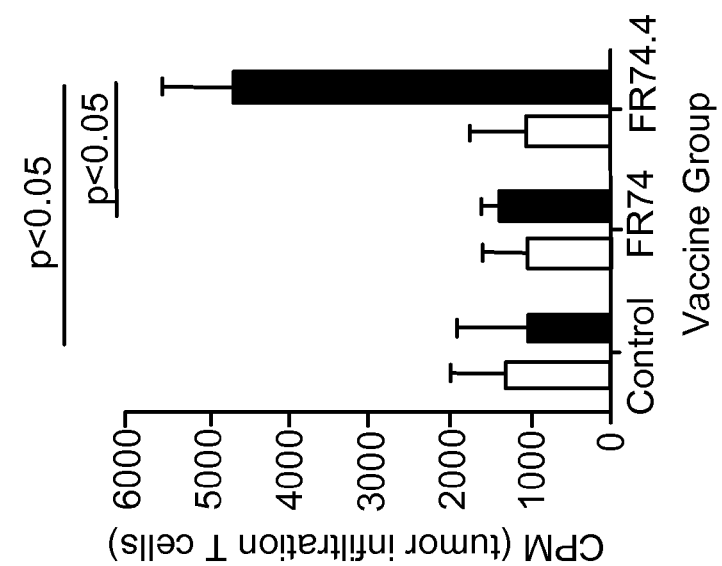
Figure 34A:
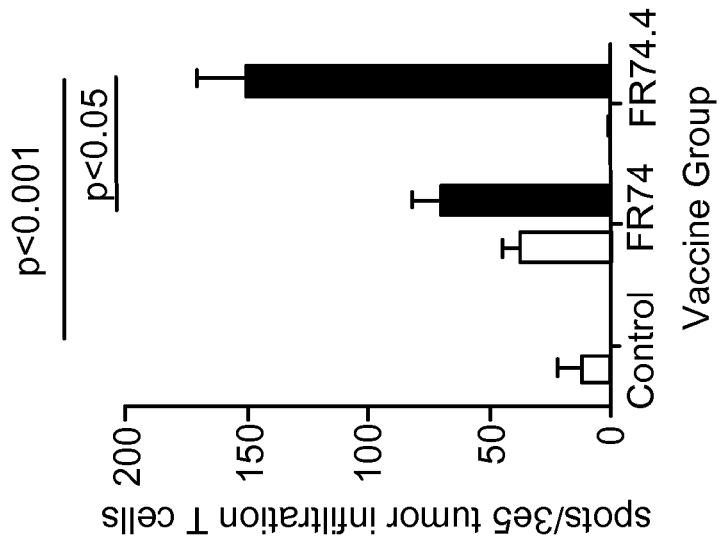

In addition, the weight of the greater omentum (a surrogate of total tumor burden) 50 days following last immunization was measured (FIG. 34C). These results demonstrate that immunization of ovarian cancer-bearing animals with nested epitopes results in tumor eradication and infiltration of FR74-specific T cells that retain proliferation.

Summary

One of the unique features of this model system worth further discussion is the peptide and species, and tumor type independence of this approach, an aspect that is not often seen in other therapeutics. For example, in melanoma, TIL are relatively amendable to ex vivo expansion using non-specific methods, a fact that does not hold true for many other solid cancers. Therefore, the successes of adoptive T cell therapy in melanoma cannot be translated to other cancers without the further development of novel ex vivo expansion methodologies.

In addition to adoptive T cell therapy, the methods and materials provided herein can also be extended in other directions as well. Epitope nesting permits dissection of methods involved in the requirements for activation of naïve T cells from mixed T cell pools that would not ordinarily be achievable under other conditions. Modeling ex vivo expansion and adoptive T cell therapy has relied heavily on TCR transgenic mice which are important for the dissection of some but not all mechanisms of T cell activation. A good example of this important aspect is the chemokine studies described herein.

Figure 30:
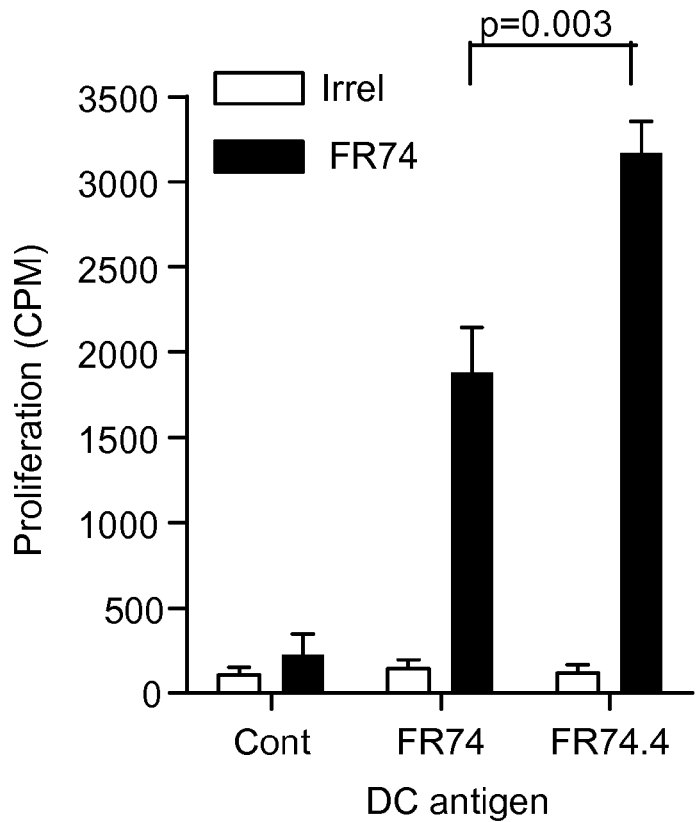
FIG. 30. DC pulsed with modified polypeptides are more immunogenic than FR74-pulsed DC. Panel shows proliferation results of splenocytes from untreated mice (Cont) or mice immunized with DC pulsed with FR74 or FR74.4. Each bar shows mean (±s.e.m.) proliferation response of triplicate samples. Control=DC pulsed with media.
Figure 31:
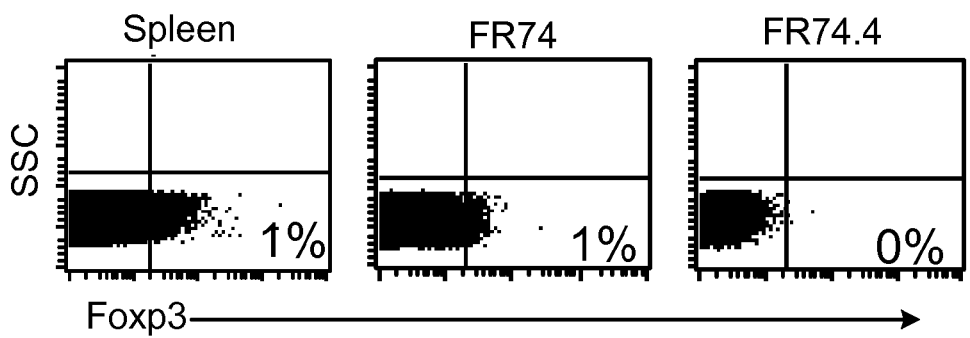
FIG. 31. Epitope nesting blocks expansion of Foxp3+ T cells. Flow cytometry dot plots of naïve splenocytes, FR74-specific, FR74.4-specific CD4 T cell lines evaluating for FoxP3 expression. Quadrants set at isotype signal, and the lower right quadrant is percent of total cells in lymphocyte gate. T cells were derived from FVB/N mice.

Alternatively, the strategies developed herein can be applied to other fields of immunotherapy. Immunization studies revealed that these modifications can improve the immunogenicity of DC-based vaccines, which is shown in FIG. 30. In that experiment, bone-marrow derived DC were pulsed with either PBS, FR74 peptide, or FR74.4 peptide for 2 hours. The DC were washed and injected into FVB/N mice. Splenocytes were prepared at 1 week and tested for proliferation in response to native FR74 antigen with the results showing a significantly elevated proliferative response.

Other Embodiments

It is to be understood that while the invention has been described in conjunction with the detailed description

What is claimed is:

1. A method for activating T cells in a mammal, said method comprising administering a composition comprising a polypeptide to said mammal, wherein said polypeptide comprises an invariant chain amino acid sequence, an MHC class II epitope amino acid sequence, and a DC3 amino acid sequence, wherein said polypeptide is between 20 and 80 amino acids in length, wherein said invariant chain amino acid sequence comprises LRMK (SEQ ID NO:44), wherein said DC3 amino acid sequence comprises FYPSYHSTPQRP (SEQ ID NO:2), and wherein said MHC class II epitope amino acid sequence comprises KDISYLYRFNWNHCG (SEQ ID NO:1).

* * * * *

SEQUENCE LISTING

```
<160> NUMBER OF SEQ ID NOS: 44

<210> SEQ ID NO 1
<211> LENGTH: 15
<212> TYPE: PRT
<213> ORGANISM: Mus musculus

<400> SEQUENCE: 1

Lys Asp Ile Ser Tyr Leu Tyr Arg Phe Asn Trp Asn His Cys Gly
1               5                   10                  15

<210> SEQ ID NO 2
<211> LENGTH: 12
<212> TYPE: PRT
<213> ORGANISM: Artificial Sequence
<220> FEATURE:
<223> OTHER INFORMATION: DC3 amino acid sequence

<400> SEQUENCE: 2

Phe Tyr Pro Ser Tyr His Ser Thr Pro Gln Arg Pro
1               5                   10

<210> SEQ ID NO 3
<211> LENGTH: 4
<212> TYPE: PRT
<213> ORGANISM: Artificial Sequence
<220> FEATURE:
<223> OTHER INFORMATION: invariant chain amino acid sequence

<400> SEQUENCE: 3

Leu Met Arg Lys
1

<210> SEQ ID NO 4
<211> LENGTH: 4
<212> TYPE: PRT
<213> ORGANISM: Artificial Sequence
<220> FEATURE:
<223> OTHER INFORMATION: furin sensitive linker

<400> SEQUENCE: 4

Arg Ala Arg Arg
1

<210> SEQ ID NO 5
<211> LENGTH: 20
<212> TYPE: PRT
<213> ORGANISM: Artificial Sequence
<220> FEATURE:
<223> OTHER INFORMATION: synthetically generated polypeptide
<220> FEATURE:
<221> NAME/KEY: VARIANT
<222> LOCATION: 5
<223> OTHER INFORMATION: Xaa = Epsilon amino-n-valeric

<400> SEQUENCE: 5

Leu Arg Met Lys Xaa Lys Asp Ile Ser Tyr Leu Tyr Arg Phe Asn Trp
 1               5                   10                  15

Asn His Cys Gly
            20

<210> SEQ ID NO 6
<211> LENGTH: 31
<212> TYPE: PRT
```

```
<213> ORGANISM: Artificial Sequence
<220> FEATURE:
<223> OTHER INFORMATION: synthetically generated polypeptide

<400> SEQUENCE: 6

Lys Asp Ile Ser Tyr Leu Tyr Arg Phe Asn Trp Asn His Cys Gly Arg
 1               5                  10                  15

Ala Arg Arg Phe Tyr Pro Ser Tyr His Ser Thr Pro Gln Arg Pro
            20                  25                  30

<210> SEQ ID NO 7
<211> LENGTH: 36
<212> TYPE: PRT
<213> ORGANISM: Artificial Sequence
<220> FEATURE:
<223> OTHER INFORMATION: synthetically generated polypeptide
<220> FEATURE:
<221> NAME/KEY: VARIANT
<222> LOCATION: 5
<223> OTHER INFORMATION: Xaa = Epsilon-amino-n-valeric acid

<400> SEQUENCE: 7

Leu Arg Met Lys Xaa Lys Asp Ile Ser Tyr Leu Tyr Arg Phe Asn Trp
 1               5                  10                  15

Asn His Cys Gly Arg Ala Arg Arg Phe Tyr Pro Ser Tyr His Ser Thr
            20                  25                  30

Pro Gln Arg Pro
        35

<210> SEQ ID NO 8
<211> LENGTH: 31
<212> TYPE: PRT
<213> ORGANISM: Artificial Sequence
<220> FEATURE:
<223> OTHER INFORMATION: synthetically generated polypeptide

<400> SEQUENCE: 8

Lys Asp Ile Ser Tyr Leu Tyr Arg Phe Asn Trp Asn His Cys Gly Val
 1               5                  10                  15

Arg Val Val Phe Tyr Pro Ser Tyr His Ser Thr Pro Gln Arg Pro
            20                  25                  30

<210> SEQ ID NO 9
<211> LENGTH: 31
<212> TYPE: PRT
<213> ORGANISM: Artificial Sequence
<220> FEATURE:
<223> OTHER INFORMATION: synthetically generated polypeptide

<400> SEQUENCE: 9

Lys Ile Asp Ser Tyr Leu Tyr Arg Phe Asn Trp Asn His Cys Gly Arg
 1               5                  10                  15

Arg Arg Arg Phe Tyr Pro Ser Tyr His Ser Thr Pro Gln Arg Pro
            20                  25                  30

<210> SEQ ID NO 10
<211> LENGTH: 31
<212> TYPE: PRT
<213> ORGANISM: Artificial Sequence
<220> FEATURE:
<223> OTHER INFORMATION: synthetically generated polypeptide

<400> SEQUENCE: 10

Lys Asp Ile Ser Tyr Leu Tyr Arg Phe Asn Trp Asn His Cys Gly Arg
 1               5                  10                  15
```

```
Lys Arg Arg Phe Tyr Pro Ser Tyr His Ser Thr Pro Gln Arg Pro
            20                  25                  30
```

<210> SEQ ID NO 11
<211> LENGTH: 33
<212> TYPE: PRT
<213> ORGANISM: Artificial Sequence
<220> FEATURE:
<223> OTHER INFORMATION: synthetically generated polypeptide

<400> SEQUENCE: 11

```
Lys Asp Ile Ser Tyr Leu Tyr Arg Phe Asn Trp Asn His Cys Gly Arg
1               5                   10                  15

Ala Arg Tyr Lys Arg Phe Tyr Pro Ser Tyr His Ser Thr Pro Gln Arg
            20                  25                  30

Pro
```

<210> SEQ ID NO 12
<211> LENGTH: 6
<212> TYPE: PRT
<213> ORGANISM: Artificial Sequence
<220> FEATURE:
<223> OTHER INFORMATION: cleavage site

<400> SEQUENCE: 12

```
Arg Ala Arg Tyr Lys Arg
1               5
```

<210> SEQ ID NO 13
<211> LENGTH: 30
<212> TYPE: PRT
<213> ORGANISM: Artificial Sequence
<220> FEATURE:
<223> OTHER INFORMATION: synthetically generated polypeptide

<400> SEQUENCE: 13

```
Lys Asp Ile Ser Tyr Leu Arg Phe Asn Trp Asn His Cys Gly Arg Ala
1               5                   10                  15

Arg Arg Phe Tyr Pro Ser Tyr His Ser Thr Pro Gln Arg Pro
            20                  25                  30
```

<210> SEQ ID NO 14
<211> LENGTH: 28
<212> TYPE: PRT
<213> ORGANISM: Artificial Sequence
<220> FEATURE:
<223> OTHER INFORMATION: synthetically generated polypeptide

<400> SEQUENCE: 14

```
Lys Asp Ile Ser Tyr Leu Tyr Arg Phe Asn Trp Asn His Cys Gly Arg
1               5                   10                  15

Ala Arg Arg Ser Tyr His Ser Thr Pro Gln Arg Pro
            20                  25
```

<210> SEQ ID NO 15
<211> LENGTH: 25
<212> TYPE: PRT
<213> ORGANISM: Artificial Sequence
<220> FEATURE:
<223> OTHER INFORMATION: synthetically generated polypeptide

<400> SEQUENCE: 15

```
Lys Asp Ile Ser Tyr Leu Tyr Arg Phe Asn Trp Asn His Cys Gly Arg
1               5                   10                  15
```

```
Ala Arg Arg Ser Thr Pro Gln Arg Pro
            20                  25

<210> SEQ ID NO 16
<211> LENGTH: 22
<212> TYPE: PRT
<213> ORGANISM: Artificial Sequence
<220> FEATURE:
<223> OTHER INFORMATION: synthetically generated polypeptide

<400> SEQUENCE: 16

Lys Asp Ile Ser Tyr Leu Tyr Arg Phe Asn Trp Asn His Cys Gly Arg
1               5                   10                  15

Ala Arg Arg Gln Arg Pro
            20

<210> SEQ ID NO 17
<211> LENGTH: 8
<212> TYPE: PRT
<213> ORGANISM: Artificial Sequence
<220> FEATURE:
<223> OTHER INFORMATION: invariant chain (Ii) amino acid sequences

<400> SEQUENCE: 17

Leu Arg Met Lys Leu Pro Lys Ser
1               5

<210> SEQ ID NO 18
<211> LENGTH: 11
<212> TYPE: PRT
<213> ORGANISM: Artificial Sequence
<220> FEATURE:
<223> OTHER INFORMATION: invariant chain (Ii) amino acid sequences

<400> SEQUENCE: 18

Leu Arg Met Lys Leu Pro Lys Ser Ala Lys Pro
1               5                   10

<210> SEQ ID NO 19
<211> LENGTH: 14
<212> TYPE: PRT
<213> ORGANISM: Artificial Sequence
<220> FEATURE:
<223> OTHER INFORMATION: invariant chain (Ii) amino acid sequences

<400> SEQUENCE: 19

Leu Arg Met Lys Leu Pro Lys Ser Ala Lys Pro Val Ser Lys
1               5                   10

<210> SEQ ID NO 20
<211> LENGTH: 15
<212> TYPE: PRT
<213> ORGANISM: Artificial Sequence
<220> FEATURE:
<223> OTHER INFORMATION: MHC class II epitopes sequences

<400> SEQUENCE: 20

Leu Leu Thr Phe Trp Asn Pro Pro Thr Thr Ala Lys Leu Thr Ile
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: MHC class II epitopes sequences
```

```
<400> SEQUENCE: 21

Tyr Leu Trp Trp Val Asn Asn Gln Ser Leu Pro Val Ser Pro Arg
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: MHC class II epitopes sequences

<400> SEQUENCE: 22

Arg Thr Thr Val Lys Thr Ile Thr Val Ser Ala Glu Leu Pro Lys
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: MHC class II epitopes sequences

<400> SEQUENCE: 23

Tyr Ala Cys Phe Val Ser Asn Leu Ala Thr Gly Arg Asn Asn Ser
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: MHC class II epitopes sequences

<400> SEQUENCE: 24

Asn Leu Glu Leu Thr Tyr Leu Pro Thr Asn Ala Ser Leu Ser Phe
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: MHC class II epitopes sequences

<400> SEQUENCE: 25

His Asn Gln Val Arg Gln Val Pro Leu Gln Arg Leu Arg Ile Val
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: MHC class II epitopes sequences

<400> SEQUENCE: 26

Leu Ser Val Phe Gln Asn Leu Gln Val Ile Arg Gly Arg Ile Leu
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: MHC class II epitopes sequences
```

```
<400> SEQUENCE: 27

Pro Ile Lys Trp Met Ala Leu Glu Ser Ile Leu Arg Arg Arg Phe
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: MHC class II epitopes sequences

<400> SEQUENCE: 28

Leu Leu Pro Leu Leu Pro Leu Leu Leu Leu Leu Leu Gly Ala Ser
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: MHC class II epitopes sequences

<400> SEQUENCE: 29

Pro Leu Leu Leu Leu Leu Leu Gly Ala Ser Gly Gly Gly Gly Gly
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: MHC class II epitopes sequences

<400> SEQUENCE: 30

Glu Arg Gly Pro Leu Glu His Leu Tyr Ser Leu His Ile Pro Asn
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: MHC class II epitopes sequences

<400> SEQUENCE: 31

Thr Gly Lys Leu Ile Gln Gly Ala Pro Thr Ile Arg Gly Asp Pro
1               5                   10                  15

<210> SEQ ID NO 32
<211> LENGTH: 6
<212> TYPE: PRT
<213> ORGANISM: Artificial Sequence
<220> FEATURE:
<223> OTHER INFORMATION: Epsilon-amino-n-valeric acid sequences

<400> SEQUENCE: 32

Gly Gly Ser Gly Gly Ser
1               5

<210> SEQ ID NO 33
<211> LENGTH: 15
<212> TYPE: PRT
<213> ORGANISM: Homo sapiens

<400> SEQUENCE: 33

Gln Cys Arg Pro Trp Arg Lys Asn Ala Cys Cys Ser Thr Asn Thr
```

```
<210> SEQ ID NO 34
<211> LENGTH: 6
<212> TYPE: PRT
<213> ORGANISM: Artificial Sequence
<220> FEATURE:
<223> OTHER INFORMATION: linker sequence

<400> SEQUENCE: 34

Gly Gly Ser Gly Gly Ser
1               5

<210> SEQ ID NO 35
<211> LENGTH: 12
<212> TYPE: PRT
<213> ORGANISM: Artificial Sequence
<220> FEATURE:
<223> OTHER INFORMATION: linker sequence

<400> SEQUENCE: 35

Gly Gly Ser Gly Gly Ser Gly Gly Ser Gly Gly Ser
1               5                   10

<210> SEQ ID NO 36
<211> LENGTH: 18
<212> TYPE: PRT
<213> ORGANISM: Artificial Sequence
<220> FEATURE:
<223> OTHER INFORMATION: linker sequence

<400> SEQUENCE: 36

Gly Gly Ser Gly Gly Ser Gly Gly Ser Gly Gly Ser Gly Gly Ser Gly
1               5                   10                  15

Gly Ser

<210> SEQ ID NO 37
<211> LENGTH: 24
<212> TYPE: PRT
<213> ORGANISM: Artificial Sequence
<220> FEATURE:
<223> OTHER INFORMATION: linker sequence

<400> SEQUENCE: 37

Gly Gly Ser Gly Gly Ser Gly Gly Ser Gly Gly Ser Gly Gly Ser Gly
1               5                   10                  15

Gly Ser Gly Gly Ser Gly Gly Ser
            20

<210> SEQ ID NO 38
<211> LENGTH: 30
<212> TYPE: PRT
<213> ORGANISM: Artificial Sequence
<220> FEATURE:
<223> OTHER INFORMATION: linker sequence

<400> SEQUENCE: 38

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser
            20                  25                  30

<210> SEQ ID NO 39
<211> LENGTH: 36
<212> TYPE: PRT
```

```
<213> ORGANISM: Artificial Sequence
<220> FEATURE:
<223> OTHER INFORMATION: linker sequence

<400> SEQUENCE: 39

Gly Gly Ser Gly Gly Ser Gly Gly Ser Gly Gly Ser Gly Gly Ser Gly
  1               5                   10                  15

Gly Ser Gly Gly Ser Gly Gly Ser Gly Gly Ser Gly Gly Ser Gly Gly
             20                  25                  30

Ser Gly Gly Ser
         35

<210> SEQ ID NO 40
<211> LENGTH: 4
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: 2
<223> OTHER INFORMATION: Xaa = any amino acid
<220> FEATURE:
<221> NAME/KEY: VARIANT
<222> LOCATION: 3
<223> OTHER INFORMATION: Xaa = Arg or Lys

<400> SEQUENCE: 40

Arg Xaa Xaa Arg
  1

<210> SEQ ID NO 41
<211> LENGTH: 4
<212> TYPE: PRT
<213> ORGANISM: Artificial Sequence
<220> FEATURE:
<223> OTHER INFORMATION: linker sequence

<400> SEQUENCE: 41

Val Arg Val Val
  1

<210> SEQ ID NO 42
<211> LENGTH: 4
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: 1
<223> OTHER INFORMATION: Xaa = decanoly-Arg
<220> FEATURE:
<221> NAME/KEY: VARIANT
<222> LOCATION: 4
<223> OTHER INFORMATION: Xaa = Arg-CH2CL

<400> SEQUENCE: 42

Xaa Val Lys Xaa
  1

<210> SEQ ID NO 43
<211> LENGTH: 4
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
```

```
<222> LOCATION: 2
<223> OTHER INFORMATION: Xaa = any amino acid
<220> FEATURE:
<221> NAME/KEY: VARIANT
<222> LOCATION: 3
<223> OTHER INFORMATION: Xaa = Lys or Arg

<400> SEQUENCE: 43

Arg Xaa Xaa Arg
 1

<210> SEQ ID NO 44
<211> LENGTH: 4
<212> TYPE: PRT
<213> ORGANISM: Artificial Sequence
<220> FEATURE:
<223> OTHER INFORMATION: invariant chain amino acid sequence

<400> SEQUENCE: 44

Leu Arg Met Lys
 1
```